(12) United States Patent
Zafiris

(10) Patent No.: US 11,672,896 B2
(45) Date of Patent: Jun. 13, 2023

(54) CAPACITIVE PRIMING SENSOR FOR A MEDICAL FLUID DELIVERY SYSTEM

(71) Applicants: BAXTER INTERNATIONAL INC., Deerfield, IL (US); BAXTER HEALTHCARE SA, Glattpark (CH)

(72) Inventor: John Zafiris, Hawthorn Woods, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 278 days.

(21) Appl. No.: 16/986,789

(22) Filed: Aug. 6, 2020

(65) Prior Publication Data

US 2021/0038801 A1    Feb. 11, 2021

Related U.S. Application Data

(60) Provisional application No. 62/884,862, filed on Aug. 9, 2019.

(51) Int. Cl.
*A61M 1/28*      (2006.01)
*A61M 39/10*     (2006.01)

(52) U.S. Cl.
CPC ............ *A61M 1/288* (2014.02); *A61M 39/10* (2013.01); *A61M 2039/1005* (2013.01);
(Continued)

(58) Field of Classification Search
CPC ........ A61M 1/0058; A61M 1/14; A61M 1/28; A61M 1/281; A61M 1/282; A61M 1/284; A61M 1/288; A61M 1/3643–3649; A61M 5/16831; A61M 2005/1402; A61M 2205/14; A61M 2205/33; A61M 2205/3317; A61M 2205/3334;
(Continued)

(56) References Cited

U.S. PATENT DOCUMENTS

2005/0209563 A1\* 9/2005 Hopping ................. A61M 1/28
                                                     604/151
2008/0276722 A1\* 11/2008 Wiedmann ................ G01F 1/56
                                                      73/64.48
(Continued)

FOREIGN PATENT DOCUMENTS

EP            2673018 B1 \*  4/2019 .............. A61M 1/14

*Primary Examiner* — Kami A Bosworth
(74) *Attorney, Agent, or Firm* — K&L Gates LLP

(57) ABSTRACT

A capacitive priming sensor for a medical fluid delivery system is disclosed. In an example embodiment, a priming sensor includes a housing including a recessed section configured to accept a portion of a tube. The recessed section of the housing includes a first side including a first conductive plate and a member including a second conductive plate. The member is moveably connected to a second side of the recessed section for detecting insertion of the portion of the tube into the housing of the priming sensor. The recessed section also includes a third side opposing the first side. The third side includes a third conductive plate disposed across from a top portion of the first conductive plate, and a fourth conductive plate disposed across from a bottom portion of the first conductive plate. The priming sensor also includes capacitive sensors or detectors for measuring capacitances between the conductive plates.

22 Claims, 17 Drawing Sheets

(52) U.S. Cl.
CPC . *A61M 2205/0233* (2013.01); *A61M 2205/14* (2013.01); *A61M 2205/502* (2013.01); *A61M 2205/52* (2013.01)

(58) Field of Classification Search
CPC ........ A61M 2205/70; A61M 2205/702; G01D 5/24; G01D 5/241; G01D 5/2417; G01F 1/56; G01F 23/26; G01R 27/2605
See application file for complete search history.

(56) References Cited

U.S. PATENT DOCUMENTS

| | | | |
|---|---|---|---|
| 2014/0171868 A1* | 6/2014 | Zhang | A61M 5/5086 604/111 |
| 2016/0101278 A1 | 4/2016 | Norris et al. | |
| 2020/0209043 A1 | 7/2020 | Garza et al. | |

* cited by examiner

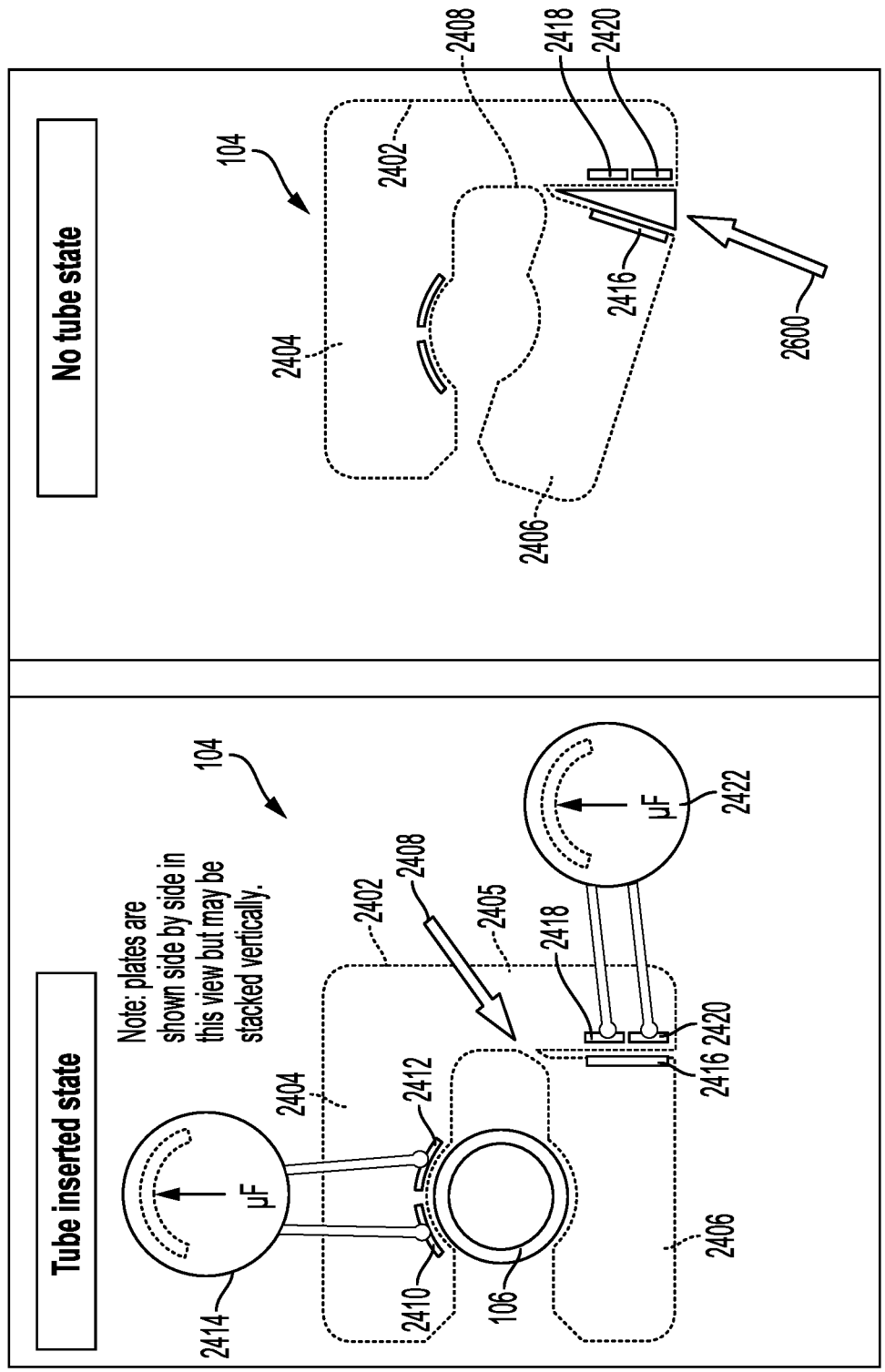

CAPACITIVE PRIMING SENSOR FOR A MEDICAL FLUID DELIVERY SYSTEM

PRIORITY CLAIM

This application claims priority to and the benefit as a non-provisional application of U.S. Provisional Patent Application No. 62/884,862, filed Aug. 9, 2019, the entire contents of which are hereby incorporated by reference and relied upon.

TECHNICAL FIELD

The present disclosure relates generally to medical fluid delivery, and more particularly to a capacitive priming sensor for an automated peritoneal dialysis ("APD") machine.

BACKGROUND

People with damaged or improperly functioning kidneys may undergo dialysis treatments to remove waste products from blood. One common type of dialysis is peritoneal dialysis ("PD"), in which a cleansing fluid, referred to as PD or dialysis fluid, is delivered to a patient's peritoneal cavity of their abdomen via a catheter. The cleansing fluid absorbs waste products during a dwell period. After the dwell period ends, the cleansing fluid is removed from the patient's peritoneal cavity along with the absorbed waste products and excess water (known as ultrafiltration), thereby compensating for the patient's improperly functioning kidneys.

An automated peritoneal dialysis ("APD") machine is used in many instances to pump a prescribed volume of a PD or dialysis fluid (e.g., a cleansing fluid) into a patient's peritoneal cavity. The APD machine is configured to permit the dialysis fluid to remain in the patient during the dwell period. After the dwell period, the APD machine drains used dialysis fluid or effluent containing waste products from the patient's peritoneal cavity. APD machines typically prime tubes and/or a tubing set that routes the dialysis fluid to the patient. The priming of the tubes and/or tubing set removes air, thereby preventing the air from being transmitted into the patient's peritoneal cavity. Priming may involve pumping the dialysis fluid to an end of a tube, such as a patient line that is later connected to the patient during the PD treatment, to remove the air within the tube.

APD machines are typically located in a patient's home, a clinic, or a hospital. In many instances, a patient prepares the APD machine for treatment by performing a priming sequence. To aid in priming the tubes, APD machines may include a sensor that detects when a tube is properly primed. Known sensors have used light to detect when the dialysis fluid has reached the end of a tube, which is indicative of a successful prime. However, fluctuations in ambient light, tube properties, tube geometries, and/or fluid type may cause the light sensor to be less accurate than desired.

SUMMARY

The example system, apparatus, and method disclosed herein are configured to provide an accurate medical fluid treatment priming sensor that is insensitive to ambient light brightness, tube properties, and/or fluid type. The dialysis priming sensor disclosed herein uses capacitance sensing. The priming sensor disclosed may include a housing that encloses electrodes and/or conductive plates that are connected to one or more sensors that measure a capacitance between the electrodes and/or conductive plates. The electrodes and/or conductive plates are positioned within the housing to form one or more capacitors. The electrodes and/or conductive plates may be located on opposite sides of the housing for detecting a fluid level based on a capacitance change when a medical fluid (e.g., dialysis fluid, dialysate, tap water, or other conductive fluids) flows through the inserted tube past the electrodes and/or conductive plates. Additionally or alternatively, at least some of the electrodes and/or conductive plates may be placed at different heights with respect to a patient tube placed in the priming sensor. The positioning of the electrodes and/or conductive plates at different heights aids in the detection of the patient tube. Placement of the patient tube in the housing of the priming sensor causes at least one electrode and/or conductive plate to move relative to other stationary electrode(s) and/or conductive plate(s) that are placed at different heights, thereby causing a change in capacitance for detecting the presence of the tube. In some embodiments, the positioning of the electrodes and/or conductive plates at different heights provides for additionally or alternatively detecting a fluid level in the patient tube.

A processor (or a control unit having one or more processors and one or more memories) analyzes the output from the one or more capacitive sensors to determine whether a patient tube is present and inserted within the priming sensor housing (e.g., detecting between a no-tube state and a dry tube state). The processor or the control unit is also configured to determine when a medical fluid such as dialysis fluid reaches a certain level in the patient tube corresponding to a successful prime (e.g., detecting between a dry state and a wet state). After detecting that a tube is present and includes a fluid (e.g., a wet tube state), the processor or the control unit is further configured to provide an indication that priming of a patient line for PD therapy is successful, which permits the priming sequence to continue/end and/or a PD treatment to begin. In some instances, the processor or the control unit may also provide an indication that the dry tube state is not present. The processor or the control unit may also be configured to provide an indication of a failed prime of the patient line if, for example, the tube itself is not detected or the wet tube state of the tube is not detected within a defined period of time.

In light of the disclosure herein and without limiting the disclosure in any way, in a first aspect of the present disclosure, which may be combined with any other aspect listed herein unless specified otherwise, a peritoneal dialysis apparatus includes a patient tube configured to receive dialysis fluid from a source of dialysis fluid, at least one pump configured to move dialysis fluid from the source to the patient tube during a priming sequence, and a priming sensor including a housing having a recessed section configured to accept a portion of the patient tube. The recessed section of the housing includes a first side including a first conductive plate, and a member including a second conductive plate. The member is moveably connected to a second side of the recessed section and configured for a desired movement upon insertion of the portion of the patient tube into the housing of the priming sensor. The recessed section also includes a third side opposing the first side. The third side includes a third conductive plate disposed across from a top portion of the first conductive plate, and a fourth conductive plate disposed across from a bottom portion of the first conductive plate. The peritoneal dialysis apparatus also includes a first capacitive sensor positioned and arranged to measure a first capacitance between the first conductive plate and the third conductive plate, a second capacitive sensor positioned and arranged to measure a second capacitance between the third conductive plate and the fourth conductive plate, and a processor configured to operate with the at least one pump, the first capacitive sensor, and the second capacitive sensor. The processor is configured to use the measured second capacitance to determine a first transition between (i) a no-tube state and (ii) a dry tube state based on a distance of the second conductive plate from the third and fourth conductive plates, use the measured first capacitance to determine a second transition between (ii) the dry tube state and (iii) a wet tube state based on a presence of fluid within the patient tube, cause the at least one pump to pump the fluid through to the patient tube for the priming sequence after the dry tube state is determined, and transmit a message indicative that the patient tube is primed after the wet tube state is determined.

In accordance with a second aspect of the present disclosure, which may be used in combination with any other aspect listed herein unless stated otherwise, the priming sensor includes a third capacitive sensor positioned and arranged to measure a third capacitance between the first conductive plate and the fourth conductive plate, and wherein the processor is configured to combine values of the first capacitance with value of the third capacitance to determine between at least one of (i) the no-tube state and (ii) the dry tube state, or (ii) the dry tube state and (iii) the wet tube state.

In accordance with a third aspect of the present disclosure, which may be used in combination with any other aspect listed herein unless stated otherwise, the second conductive plate bends or pivots when the portion of the patient tube is inserted into the housing of the priming sensor, causing the first capacitance to increase.

In accordance with a fourth aspect of the present disclosure, which may be used in combination with any other aspect listed herein unless stated otherwise, the second conductive plate is at least one of (a) positioned and arranged to electrically float, or (b) formed from a conductive plastic or a conductively painted plastic.

In accordance with a fifth aspect of the present disclosure, which may be used in combination with any other aspect listed herein unless stated otherwise, the third conductive plate is at least one of (a) formed with a width that is equal to a width of the fourth conductive plate, or (b) spaced apart from the fourth conductive plate by a distance between 0.5 millimeters and 2 centimeters.

In accordance with a sixth aspect of the present disclosure, which may be used in combination with any other aspect listed herein unless stated otherwise, the first conductive plate, the third conductive plate, and the fourth conductive plate are at least one of (a) formed as metal clips configured to secure the portion of the patient tube within the housing of the priming sensor, or (b) enclosed within the recessed section of the housing of the priming sensor.

In accordance with a seventh aspect of the present disclosure, which may be used in combination with any other aspect listed herein unless stated otherwise, the processor is configured to determine the first transition between the no-tube state and the dry tube state by determining that a change in values of the measured first capacitance is greater than a first transition threshold, and the processor is configured to determine the second transition between the dry tube state and the wet tube state by determining that a change in values of the measured second capacitance is greater than a second transition threshold.

In accordance with an eighth aspect of the present disclosure, which may be used in combination with any other aspect listed herein unless stated otherwise, at least one of the first transition threshold and the second transition threshold corresponds to at least a doubling of the respective values of the measured capacitance from a first value to a second value in less than 0.5 seconds, and wherein the second value is at least substantially constant for at least two seconds.

In accordance with a ninth aspect of the present disclosure, which may be used in combination with any other aspect listed herein unless stated otherwise, the priming sensor includes fifth and sixth conductive plates located on opposing exterior sides of the housing, and third and fourth capacitive sensors positioned and arranged to measure capacitances that change due to an external interference that is detected by at least one of the fifth or sixth conductive plates positioned relative to the first conductive plate, the third conductive plate, and the fourth conductive plate.

In accordance with a tenth aspect of the present disclosure, which may be used in combination with any other aspect listed herein unless stated otherwise, after detecting a change in the capacitance measured by the third and fourth capacitive sensors, the processor is configured to, at least one of refrain from detecting the states (i) to (iii), stop the priming sequence, or output a message that is indicative of the detected capacitance interference.

In accordance with an eleventh aspect of the present disclosure, which may be used in combination with any other aspect listed herein unless stated otherwise, the processor is further configured such that if the wet tube state is determined, a peritoneal dialysis treatment is enabled.

In accordance with a twelfth aspect of the present disclosure, which may be used in combination with any other aspect listed herein unless stated otherwise, the peritoneal dialysis apparatus includes a user interface configured to display at least one of text or a graphic corresponding to the determined state (i) to (iii).

In accordance with a thirteenth aspect of the present disclosure, which may be used in combination with any other aspect listed herein unless stated otherwise, a sensor apparatus includes a housing including a recessed section configured to accept a portion of a tube. The housing includes a first side including a first conductive plate, and a member including a second conductive plate. The member is moveably connected to a second side of the recessed section for detecting insertion of the portion of the tube into the housing. The recessed section also includes a third side opposing the first side. The third side includes a third conductive plate disposed across from a top portion of the first conductive plate, and a fourth conductive plate disposed across from a bottom portion of the first conductive plate. The sensor apparatus also includes a first capacitive sensor positioned and arranged to measure a first capacitance between the first conductive plate and the third conductive plate, and a second capacitive sensor positioned and arranged to measure a second capacitance between the third conductive plate and the fourth conductive plate.

In accordance with a fourteenth aspect of the present disclosure, which may be used in combination with any other aspect listed herein unless stated otherwise, the sensor apparatus is operable with a medical fluid delivery machine including at least one pump and a control unit operable with the first and second capacitive sensors to use the measured second capacitance to determine a first transition between (i) a no-tube state and (ii) a dry tube state based on a distance of the second conductive plate from the third and fourth conductive plates, and cause the at least one pump to pump the fluid through to the tube to conduct a priming sequence after the dry tube state is determined.

In accordance with a fifteenth aspect of the present disclosure, which may be used in combination with any other aspect listed herein unless stated otherwise, the control unit is further configured to use the measured first capacitance to determine a second transition between (ii) the dry tube state and (iii) a wet tube state based on a presence of fluid within the tube, and transmit a message indicative that the tube is primed after the wet tube state is determined.

In accordance with a sixteenth aspect of the present disclosure, which may be used in combination with any other aspect listed herein unless stated otherwise, the control unit is further configured to increment a counter each time the wet tube state is determined, compare a value of the counter to a counter threshold, and determine the wet tube state when the value of the counter equals or exceeds the counter threshold.

In accordance with a seventeenth aspect of the present disclosure, which may be used in combination with any other aspect listed herein unless stated otherwise, the control unit includes the first capacitive sensor and the second capacitive sensor.

In accordance with an eighteenth aspect of the present disclosure, which may be used in combination with any other aspect listed herein unless stated otherwise, a medical fluid delivery apparatus includes a patient tube configured to receive dialysis fluid from a source of dialysis fluid, at least one pump configured to move dialysis fluid from the source to the patient tube during a priming sequence, and a priming sensor including a housing having a recessed section configured to accept a portion of the patient tube. The recessed section of the housing includes a first side including a first conductive plate, and a member including a second conductive plate. The member is moveably connected to a second side of the recessed section and configured for a desired movement upon insertion of the portion of the patient tube into the housing of the priming sensor. The recessed section also includes a third side opposing the first side. The third side includes a third conductive plate disposed across from a top portion of the first conductive plate, and a fourth conductive plate disposed across from a bottom portion of the first conductive plate. The medical fluid delivery apparatus also includes a first capacitive sensor positioned and arranged to measure a first capacitance between the first conductive plate and the third conductive plate, a second capacitive sensor positioned and arranged to measure a second capacitance between the third conductive plate and the fourth conductive plate, and a control unit configured to operate with the pump, the first capacitive sensor, and the second capacitive sensor, the processor configured to perform the priming sequence.

In accordance with a nineteenth aspect of the present disclosure, which may be used in combination with any other aspect listed herein unless stated otherwise, the control unit during the priming sequence uses the measured second capacitance to determine a first transition between (i) a no-tube state and (ii) a dry tube state based on a distance of the second conductive plate from the third and fourth conductive plates.

In accordance with a twentieth aspect of the present disclosure, which may be used in combination with any other aspect listed herein unless stated otherwise, the control unit during the priming sequence causes the at least one pump to pump the fluid through the patient tube after the dry tube state is determined.

In accordance with a twenty-first aspect of the present disclosure, which may be used in combination with any other aspect listed herein unless stated otherwise, the control unit during the priming sequence uses use the measured first capacitance to determine a second transition between (i) a dry tube state and (ii) a wet tube state based on a presence of fluid within the patient tube.

In accordance with a twenty-second aspect of the present disclosure, which may be used in combination with any other aspect listed herein unless stated otherwise, the control unit during the priming sequence transmits a message indicative that the patient tube is primed after the wet tube state is determined.

In a twenty-third aspect of the present disclosure, any of the structure, functionality, and alternatives disclosed in connection with any one or more of FIGS. 1 to 26 may be combined with any other structure, functionality, and alternatives disclosed in connection with any other one or more of FIGS. 1 to 26.

In light of the present disclosure and the above aspects, it is therefore an advantage of the present disclosure to provide an improved priming system, device, and method for a medical fluid delivery system, such as an automatic peritoneal dialysis ("APD") system.

It is another advantage of the present disclosure to accurately detect when (i) a tube is present and (ii) a fluid reaches a certain position within the tube regardless of ambient light, tube properties, and/or fluid properties.

It is yet another advantage of the present disclosure to provide a priming sensor and methodology that may be applied to different types of medical fluid delivery machines.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIGS. 24 to 26 are diagrams of the priming sensor of FIG. 1, according to another example embodiment of the present disclosure.

DETAILED DESCRIPTION

Figure 1:
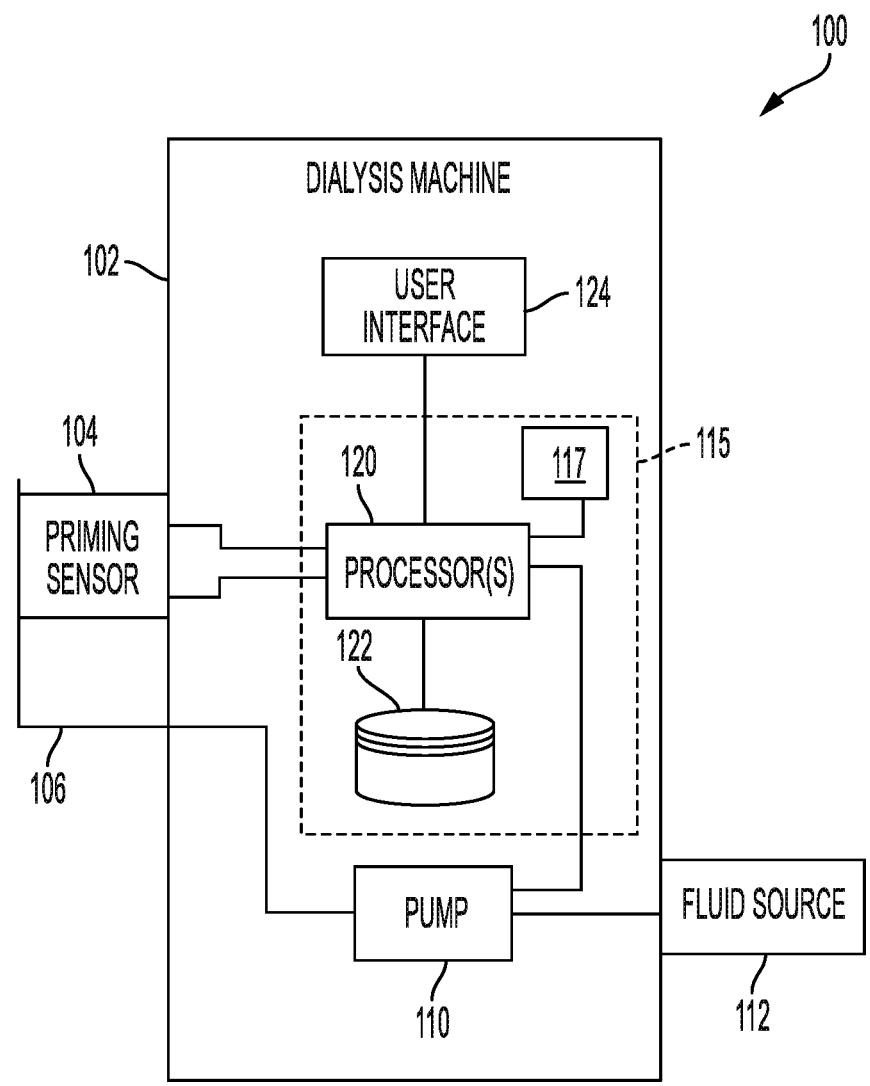
FIG. 1 is a schematic view illustrating a diagram of an example medical fluid delivery system including a priming sensor and a dialysis machine, according to an example embodiment of the present disclosure.

A medical fluid delivery system is disclosed herein. The example medical fluid delivery system may include an automated peritoneal dialysis ("APD") machine, a hemodialysis machine, a medical fluid delivery machine, or any other machine requiring one or more lines to be primed. The medical fluid delivery system includes a priming sensor configured to detect when at least one tube or line set is present and when the tube is fully primed with an appropriate fluid, such as fresh dialysis fluid. The priming sensor includes one or more capacitive sensors. During a priming operation, the capacitive sensors perform capacitance measurements between two or more electrodes or conductive plates. Capacitance measurement values from the one or more capacitive sensors may be compared to one or more thresholds. The comparison is used to determine different possible states of a patient tube including, for example, a no-tube state, a dry tube state, and a wet tube state.

In some examples, the medical fluid delivery system is configured such that if a no-tube state is detected, the medical fluid delivery system provides an alert indicative that a patient tube needs to be inserted into the priming sensor. The medical fluid delivery system may prevent the priming of the patient tube until the tube is detected by the priming sensor. If a dry tube state is detected, the medical fluid delivery system may begin and/or continue a priming sequence by pumping a fluid from a fluid source into the patient tube. If a wet tube state is detected, the medical fluid delivery system may stop the pumping of the priming fluid and/or end the priming sequence. In some embodiments, the medical fluid delivery system may be configured to confirm the wet tube state by detecting the wet tube state multiple times (e.g., between two and ten times in rapid succession to validate the wet tube state) before priming ends.

In some embodiments, the priming sensor disclosed herein includes a housing having a recessed section configured to accept and/or hold a patient tube or line set. At least some of the electrodes and/or conductive plates are located on opposite sides of the recessed section. As such, the electrodes and/or conductive plates are located on opposite sides of a patient tube when the tube is inserted into the priming sensor. Placement of the tube in the priming sensor causes a capacitance to change between the electrodes. In some embodiments, an electrode and/or conductive plate may be placed on a retaining clip that is located within the recessed section. Placement of the patient tube within the priming sensor causes the retaining clip to move toward at least one stationary electrode or conductive plate located in the recessed section of the housing. The movement of the clip caused by the insertion of the patient tube causes a change in capacitance, thereby providing for detection of the patient tube in the priming sensor.

Additionally, at least some of the electrodes and/or conductive plates are located at different heights of the housing of the priming sensor. The electrodes and/or conductive plates are separated by at least one gap. The positioning of the electrodes and/or conductive plates at different heights enables a fluid level to be determined based on a capacitance change when a dialysis fluid flows through the inserted tube and past the electrodes and/or conductive plates. The capacitance increases when the dialysis fluid flows between the electrodes and/or conductive plates because an effective distance between the electrodes or plates is reduced when a fluid replaces air between the electrodes or plates.

The example system, method, and apparatus disclosed herein provide an improvement over known priming sensors that detect a tube state using light. Known light-based priming sensors activate all of the light emitters individually. The emitters are activated to have the same brightness level. The detected light from each emitter is compared to a separate threshold (or combined into a ratio and compared to a threshold), where a tube state is determined based on a weighted average of the threshold comparisons. Increases in ambient light decrease the sensor's ability to discern brightness levels corresponding to the different tube states.

In contrast to known sensors, the example system, method, and apparatus disclosed herein, uses capacitive sensing to detect tube state. Capacitive sensing is not affected by ambient light, environmental contamination, bubbles in a priming fluid, tube thickness, or tube clarity/transparency. As a result, the capacitive sensing used by the priming sensor disclosed herein is not prone to false state detection due to these common problems. Additionally, capacitance detection for each of the states has a relatively high signal to noise ratio, e.g., greater than 1000:1. The example capacitive sensors disclosed herein may seal or otherwise enclose their electrodes, conductive plates, and other electronics within a sensor housing, thereby preventing fluid ingress and the issues that arise if the dialysis fluid contacts the electronics. Capacitive sensors also have fewer parts with fewer tolerance requirements compared to light-based sensors, and may therefore be less expensive to manufacture.

In some embodiments, the priming sensor may be configured to detect electrical interference from, for example, an operator. Generally, since humans affect electric fields, placement of an operator's hand near the priming sensor may cause measured capacitance to change. Similarly, placement of a user device, such as a smartphone near the priming sensor may cause the electric field to change, thereby changing the capacitance measurement. In some embodiments, a processor or control unit for the priming sensor is configured to detect significant variations in capacitance measurements. The processor or control unit may be configured to detect spikes and sharp drops in capacitance over relatively short periods of time, such as less than one or two seconds, which are indicative of the presence of a hand or electronic device. In response to such a detection, the processor or the control unit may refrain from concluding that a tube state change has occurred until the electrical interference is removed. In some instances, the processor or the control unit may also provide an error message on a display screen of the medical device indicating the detected interference and possibly provide an instruction to remove or eliminate the interference.

Additionally or alternatively, the priming sensor may be configured to prevent the external electrical interference. For instance, a housing of the priming sensor may include shielding, such as metallic plates, carbon filled conductive plastic, metal plated plastic, plastic sprayed with conductive paint, etc. The shielding prevents electrical interference from reaching the capacitive electrodes or conductive plates. In other instances, the priming sensor may include an additional capacitive electrode or conductive plate that is positioned adjacent to an external side of the housing of the priming sensor. The additional capacitive electrode or conductive plate is configured to detect a change in electrical field external to the priming sensor. The processor or the control unit for the priming sensor may, for example, subtract the detected change in capacitance due to the external source from the capacitance change detected within the recessed section for determining a tube state.

The example disclosure refers to peritoneal dialysis and priming a patient tube. It should be appreciated that the example system, apparatus, and method disclosed herein can be provided to operate with any type of dialysis machine, including a hemodialysis machine or a continuous replacement treatment machine. Moreover, the improved priming sensing discussed herein is not limited to dialysis, and may be used with any type of medical fluid machine, such as a medical delivery machine (e.g., an infusion pump). Further, while the disclosure relates to a patient tube, in other examples, other tubes may be primed using a priming sensor of the present disclosure, such as a heating tube, a drain tube, a medical fluid source tube, etc. Further, while the disclosure references priming a tube using dialysis fluid, it should be appreciated that the example system, apparatus, and method may operate with any type of medical fluid, including an intravenous drug, saline, renal therapy fluid, blood, sterile water, etc. Additionally, the improved sensing may be used for any purpose in which it is desired to know whether a tube is present or not and if so, whether the tube contains a liquid.

Further, while the disclosure refers to capacitive sensors, it should be appreciated that other sensors could be used. For example, the capacitive sensing disclosed herein could be replaced with inductive sensors. Moreover, the capacitive sensors may be replaced and/or used in conjunction with pressure sensors, radio-frequency ("RF") sensors, proximity detection sensors, etc.

Dialysis System Embodiment

Referring now to the drawings, FIG. 1 illustrates an example medical fluid delivery system 100, according to an example embodiment of the present disclosure. The medical fluid delivery system 100 in the illustrated embodiment includes a dialysis machine 102 configured to provide renal failure therapy to one or more patients. Renal failure therapy helps a patient balance water and minerals. Renal failure therapy also helps excrete daily metabolic load by removing a patient's toxic end products of nitrogen metabolism (urea, creatinine, uric acid, and others), which accumulate in blood and tissue. Renal failure therapy for the replacement of kidney function is critical to many people because the treatment is life saving.

In some examples, the dialysis machine 102 is an APD machine. The example dialysis machine 102 is configured to deliver dialysis fluid into a patient's peritoneal cavity via a catheter. The dialysis fluid contacts the peritoneal membrane of the peritoneal cavity for a period of time, which is referred to as a dwell period. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, such as the dialysis machine 102, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid bags.

APD machines pump used or spent dialysis fluid from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

In some embodiments, the dialysis machine 102 may be configured to perform hemodialysis ("HD"). During HD, the dialysis machine 102 is configured to use diffusion to remove waste products from a patient's blood. A diffusive gradient occurs across the semi-permeable dialyzer between a patient's blood and an electrolyte solution called dialysate or dialysis fluid to cause diffusion. Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

The example dialysis machine 102 may be located in a center, a hospital, or a patient's home. A trend towards home dialysis exists today in part because home dialysis can be performed daily, offering therapeutic benefits over in-center dialysis treatments, which occur typically bi- or tri-weekly. Studies have shown that frequent treatments remove more toxins and waste products than a patient receiving less frequent but perhaps longer treatments. A patient receiving treatments more frequently does not experience as much of a down cycle as does an in-center patient, who has built-up two or three days' worth of toxins prior to treatment. In certain areas, the closest dialysis center can be many miles from the patient's home causing door-to-door treatment time to consume a large portion of the day. Home dialysis may take place overnight or during the day while the patient relaxes, works or is otherwise productive. Much of the appeal of a home treatment for the patient revolves around the lifestyle flexibility provided by allowing the patient to perform treatment in his or her home largely according to his or her own schedule.

Any of the above dialysis modalities performed by the dialysis machine 102 may be run on a scheduled basis and may require a start-up procedure. For example, dialysis patients typically perform treatment on a scheduled basis, such as every other day, daily, etc. Dialysis treatment machines typically require a certain amount of time before treatment for setup, for example, to run a priming and/or disinfection procedure. During a priming procedure, a fluid is pumped through one or more dialysis tubes/lines and/or cassettes to remove air and/or in-line particulates. Priming dialysis tubes/lines and/or cassettes prevents air and/or the particulates from coming into contact with the patient.

The example dialysis machine 102 of FIG. 1 includes a priming sensor 104 configured to detect appropriate priming of at least one dialysis tube/line. In the illustrated embodiment, the priming sensor 104 is configured to detect priming of a patient tube 106. In other embodiments, the priming sensor 104 is configured for priming of additional or alternative tubes, such as to-patient tubes/from-patient tubes of a continuous flow peritoneal dialysis set, drain tubes, heating tubes, source fluid tubes, concentrate tubes, etc. For HD, the priming sensor 104 may be configured to prime an extracorporeal circuit, a to-dialyzer tube, a from-dialyzer tube, a source tube, a blood tube, a saline tube, and/or a drain tube. The patient tube 106 may be made of any suitable medical grade material, such as polyvinyl chloride ("PVC"), silicone, or other non-PVC material. The tube 106 in one embodiment has an inner or outer diameter that is equal to or less than 6 millimeters or 12 millimeters.

The dialysis machine 102 in the illustrated embodiment includes at least one pump 110 configured to move dialysis fluid from a fluid source 112 to the patient tube 106. The pump 110 may include any type of pump, including a peristaltic pump, a rotary pump, a gear pump, a platen, a linear actuator pump, a diaphragm pump, etc. The pump 110 is operated to prime the patient tube 106 with dialysis fluid. The pump 110 is also operated to provide dialysis fluid from the fluid source 112 to a patient when the patient tube 106 is connected to a catheter that is inserted into a patient's peritoneal cavity. Priming may alternatively or additionally be performed using gravity where, for example, a source of fluid is provided at a head height above the dialysis machine 102.

In some embodiments, the dialysis machine 102 includes a disposable cassette, which is connected fluidly to the patient tube 106 and other tubing such as fill tubes and drain tubes. The cassette may include one or more flexible membranes and associated chambers that operate with valves and/or pumps in the dialysis machine 102. Priming the patient tube 106 may include priming the disposable cassette with the dialysis fluid in addition to the one or more connected tubes.

The fluid source 112 may include one or more containers of pre-mixed dialysis fluid. In some embodiments, the fluid source 112 may include containers or reservoirs of concentrate that have been mixed with pure water to form dialysis fluid. Additionally or alternatively, the fluid source 112 may include an on-line source, such as a source of purified water that is mixed with one or more concentrates to form dialysis fluid. Moreover, in some examples, the fluid source 112 may include a fluid preparation device that provides prepared dialysis fluid to the dialysis machine 102 via one or more fluid connections.

The example dialysis machine 102 of FIG. 1 also includes one or more processors 120 and one or more memories 122 that form a control unit 115. The processor(s) 120 may include any type of device capable of processing inputs and performing one or more calculations to determine one or more outputs. The processor(s) 120 may include a microcontroller, a microprocessor unit ("MPU"), a controller, an application specific integrated circuit ("ASIC"), a central processing unit included on one or more integrated circuits, etc. In some embodiments, the processor(s) 120 may include a first processing device that is configured to process measured capacitances and determine a tube state and a second processing device that is configured to perform dialysis operations using, in part, data and instructions from the first processing device that are indicative of the tube state.

The memory 122 may include any volatile or non-volatile data/instruction storage device. The memory 122 may include, for example, flash memory, random-access memory ("RAM"), read-only memory ("ROM"), Electrically Erasable Programmable Read-Only Memory ("EEPROM"), etc. The example memory 122 is configured to store one or more instructions executable by the processor 120 to cause the processor 120 to perform operations disclosed herein. The instructions may be part of one or more software programs or applications. References herein to the processor 120 being configured to perform an operation may include embodiments in which the memory 122 stores instructions that are configured to cause the processor 120 to perform the described operation. The processor 120 and the memory are collectively referred to as a control unit 115.

The example memory 122 is configured to store instructions that cause the processor(s) 120 to detect a tube state and/or operate the dialysis machine 102. The processor 120

(or a second processor of the dialysis machine 102) may also provide control signals or instructions to the pump 110 and/or cause the pump 110 to move dialysis fluid from the fluid source 112 to the patient tube 106 during a priming sequence and during a dialysis treatment. The operations performed by the processor(s) 120, when called upon to do so, also include periodically (e.g., every 1 millisecond ("ms"), 10 ms, 250 ms, 100 ms, 500 ms, 1 second, 2 seconds, etc.) and/or continually measuring a capacitance between electrodes and/or conductive plates of the priming sensor 104. As disclosed herein, the memory 122 includes instructions that cause the processor 120 to analyze values indicative of measured capacitance of the priming sensor 104 to determine a state of the patient tube 106.

The example processor 120 is also configured to transmit one or more messages to a user interface 124 of the dialysis machine 102 for displaying or otherwise conveying information on a display screen, such as a touchscreen. The processor 120 may cause the user interface 124 to display instructions to a patient for preparing the dialysis machine 102 for a treatment, including actions to prepare for a priming sequence. The user interface 124 may also display or otherwise convey indications that are indicative of alert conditions, such as a warning to place the patient tube 106 within the priming sensor 104 or to connect the patient tube 106 to a catheter after a priming sequence has been completed. The user interface 124 may include a touchscreen overlay and/or electromechanical actuators, buttons, and/or switches to enable an operator to input information. An input received by the user interface 124 may include a prompt from an operator to begin a priming sequence or a dialysis treatment.

In some embodiments, the processor 120 and/or the memory 122 are included within the control unit 115. Further, the control unit 115 may include one or more capacitive sensors 117 that operate with the priming sensor 104. In some examples, the sensors 117 are separate from the processor 120. In other examples, the sensors 117 may be included within the processor 120.

It should be appreciated that the dialysis machine 102 may include additional components for system preparation and/or performing dialysis treatments. The additional components may include pump actuators, compressors, pressure tanks, pneumatic equipment, valve actuators, heaters, online fluid generation equipment, fluid pressure sensors, fluid temperature sensors, conductivity sensors, and air detection sensors. The dialysis machine 102 may additionally or alternatively include blood leak detection sensors, filters, dialyzers, balance chambers, sorbent cartridges, etc. In addition, the dialysis machine 102 may include one or more network connections (e.g., an Ethernet connection) to enable the processor 120 to receive data/prescriptions and transmit dialysis therapy status information to a remote or centralized server via a network (e.g., the Internet). In an embodiment, the control unit 115 using the processor 120 may create a data structure or log that includes an indication of priming, detection of patient tube state changes, a date/time when the state change occurred, and/or indications of alarms provided.

Priming Sensor Embodiments

Figure 2:
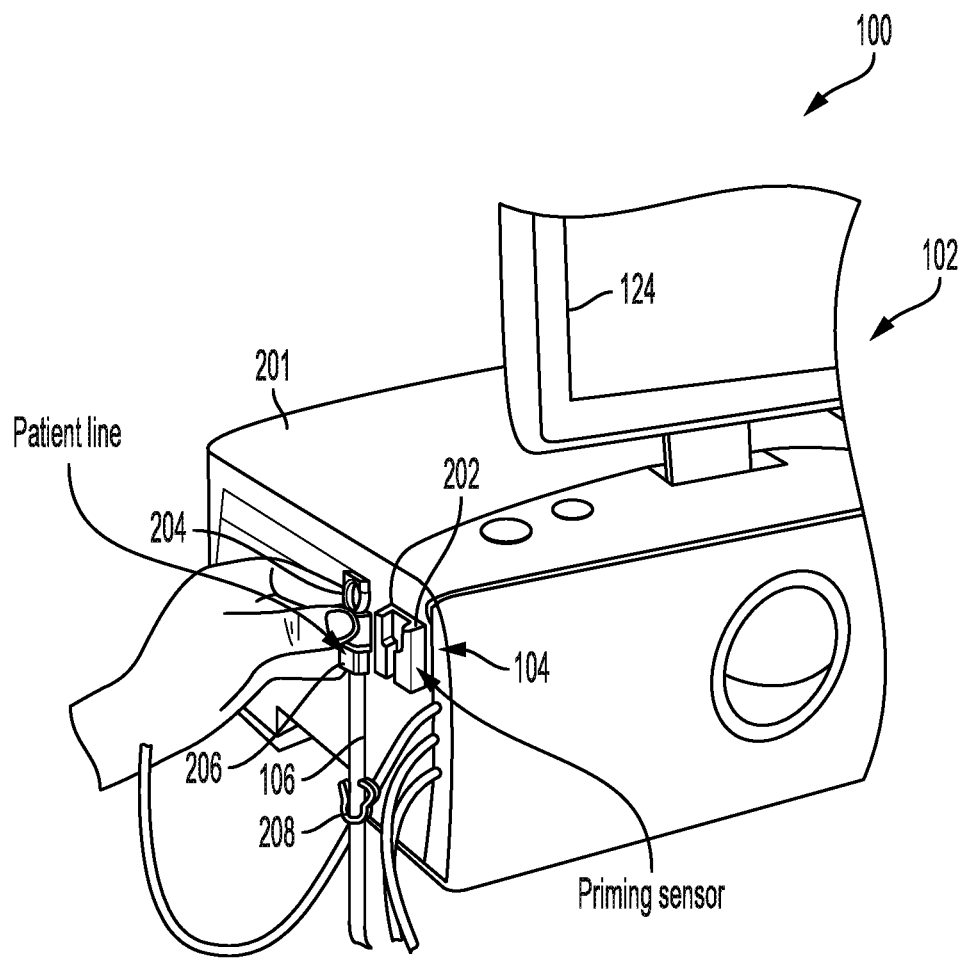
FIG. 2 is a perspective view illustrating a diagram of the priming sensor relative to the dialysis machine of the example medical fluid delivery system of FIG. 1, according to an example embodiment of the present disclosure.

FIG. 2 illustrates an embodiment of the priming sensor 104 positioned relative to the dialysis machine 102 of the example medical fluid delivery system 100 of FIG. 1, according to an example embodiment of the present disclosure. In the illustrated example, the priming sensor 104 is provided on or otherwise connected to a housing 201 of the dialysis machine 102 via a housing 202 of the priming sensor 104. The housing 202 is configured to retain the patient tube 106 in place to enable measurements to be made. The housing 202 may include or form a clip configured to engage the patient tube 106, which may include a cap 204. For example, the housing 202 may include a cylindrical opening that corresponds to or aligns with corresponding structure of the tube 106 to retain the tube in place. A patient inserts, e.g., snap-fits the tube 106 into the housing 202 by placing the patient tube 106 into an open channel of the housing 202. The patient, in one embodiment, lowers the tube 106 until it is seated within the housing 202. While the housing 202 is shown as being located on a side of the dialysis machine 102, in other embodiments, the housing 202 may be located on a top, front, back, and/or opposing surface of the dialysis machine.

The example cap 204 is configured to mechanically connect to an end connector 206 of the patient tube 106. The cap 204 optionally includes a hydrophobic vent or filter that permits air to vent from the patient tube 106 during a priming sequence. The vent or filter, in an embodiment, helps prevents fluid from overflowing out of the patient tube 106. However, overfilling the tube 106 may cause the cap 204 to separate from the tube. The priming sensor 104 is configured to detect when fluid reaches the end connector 206 (or just below the connector 206) of the patient tube 106 to determine when fluid pumping or gravity priming should stop. In such a case, the hydrophobic vent may not be needed. After a priming sequence has been completed, a patient may disconnect the cap 204 from the end connector 206. The patient may then connect the end connector 206 of the patient tube 106 to a catheter, which is fluidly connected to the patient's peritoneal cavity.

FIG. 2 also illustrates that the patient tube 106 may include a tube clamp 208. The tube clamp 208 may be clamped to the tube 106 prior to priming to prevent fluid from unintentionally exiting the patient tube 106. The tube clamp 208 is disengaged prior to the priming sequence but may be clamped after priming while the patient connects the end connector 206 to a catheter (or related transfer set) to begin treatment. The tube clamp 208 may optionally be omitted.

Figure 3:
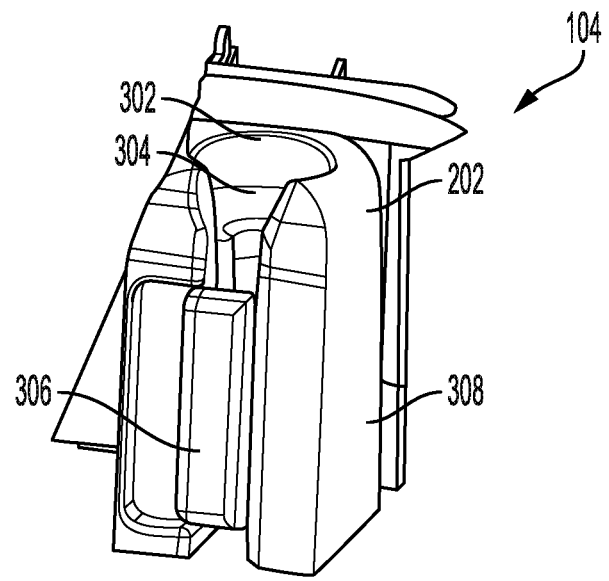
FIG. 3 is a perspective view illustrating a diagram of a housing of the priming sensor of FIGS. 1 and 2, according to an example embodiment of the present disclosure.

FIG. 3 illustrates the housing 202 of the priming sensor 104 of FIGS. 1 and 2, according to an example embodiment of the present disclosure. The example housing 202 of FIG. 3 includes a recessed section 302 configured to accept and engage the tube 106. The recessed section 302 may have a u-shape or semi-circular shape that at least partially encircles the tube 106. The recessed section 302 in the illustrated embodiment includes a lip 304 configured to receive and secure the tube 106 in place. The recessed section 302 includes walls configured to enclose or otherwise encase one or more electrodes and/or conductive plates, which are discussed in more detail in connection with FIGS. 6 to 10.

The example housing 202 also includes a retainer clip 306 (e.g., a member). The example retainer clip 306 includes a conductive plate or electrode with an end that is connected to an interior section or the recessed section 302. The retainer clip 306 is configured to hold the tube 106 within the lip 304 of the housing 202 when the tube 106 is inserted. As such, the example retainer clip 306 is configured to cause the tube 106 to be properly aligned within the priming sensor 104. The retainer clip 306 may be configured to provide a compressive force to further retain the tube 106 in place after insertion. As discussed in more detail in connection with FIG. 9, the movement of the retainer clip 306 towards the recessed section 302 when the tube 106 is inserted changes a measured capacitance, which is used to detect between a no-tube state and a dry tube state.

The example housing 202 also includes exterior walls 308. The exterior walls 308 may include one or more shields to prevent or at least reduce electrical field interference within the recessed section 302 due to external sources. Additionally or alternatively, the exterior walls 308 may enclose or otherwise encase one or more electrodes and/or conductive plates to sense changes to an electric field due to an external source, such as a smartphone or a hand of an operator.

Figure 4:
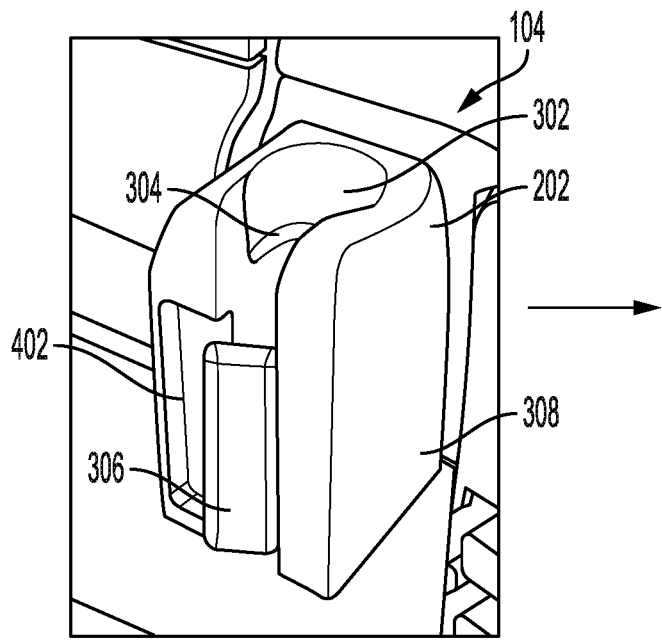
FIG. 4 is a perspective view of the priming sensor of FIGS. 1 to 3 before a tube is inserted therein, according to an example embodiment of the present disclosure.
Figure 5:
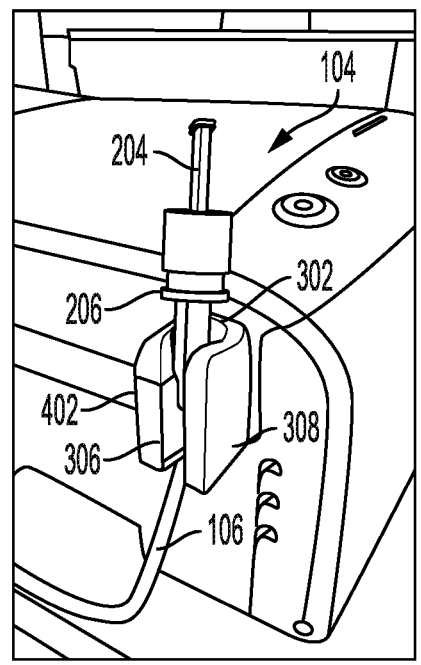
FIG. 5 is a perspective view of the priming sensor of FIG. 4 after a tube is inserted therein, according to an example embodiment of the present disclosure.

FIGS. 4 and 5 illustrate the housing 202 of the priming sensor 104 of FIG. 3, according to example embodiments of the present disclosure. FIG. 4 shows the priming sensor 104 before a tube 106 is inserted. As illustrated, the housing 202 includes a cutout area 402 configured to accommodate or otherwise receive the retainer clip 306. As such, the cutout area 402 is dimensioned to correspond to dimensions of the retainer clip 306. A spring force or other compressive force of an electrode or conductive plate holds the retainer clip 306 in a closed position.

FIG. 5 illustrates the priming sensor 104 after the tube 106 is inserted. In the illustrated example, an operator inserts the tube 106 into the priming sensor 104, which causes the retainer clip 306 to move to an open position within the cutout area 402. The tube 106 is retained within the recessed section 302 via the lip 304 and/or through a compressive force provided by the retainer clip 306. In the illustrated example of FIG. 5, the patient tube 106 includes the end connector 206 and the cap 204. The recessed section 302 of the priming sensor 104 is configured to accept or otherwise secure the end connector 206 in place.

Figure 6:
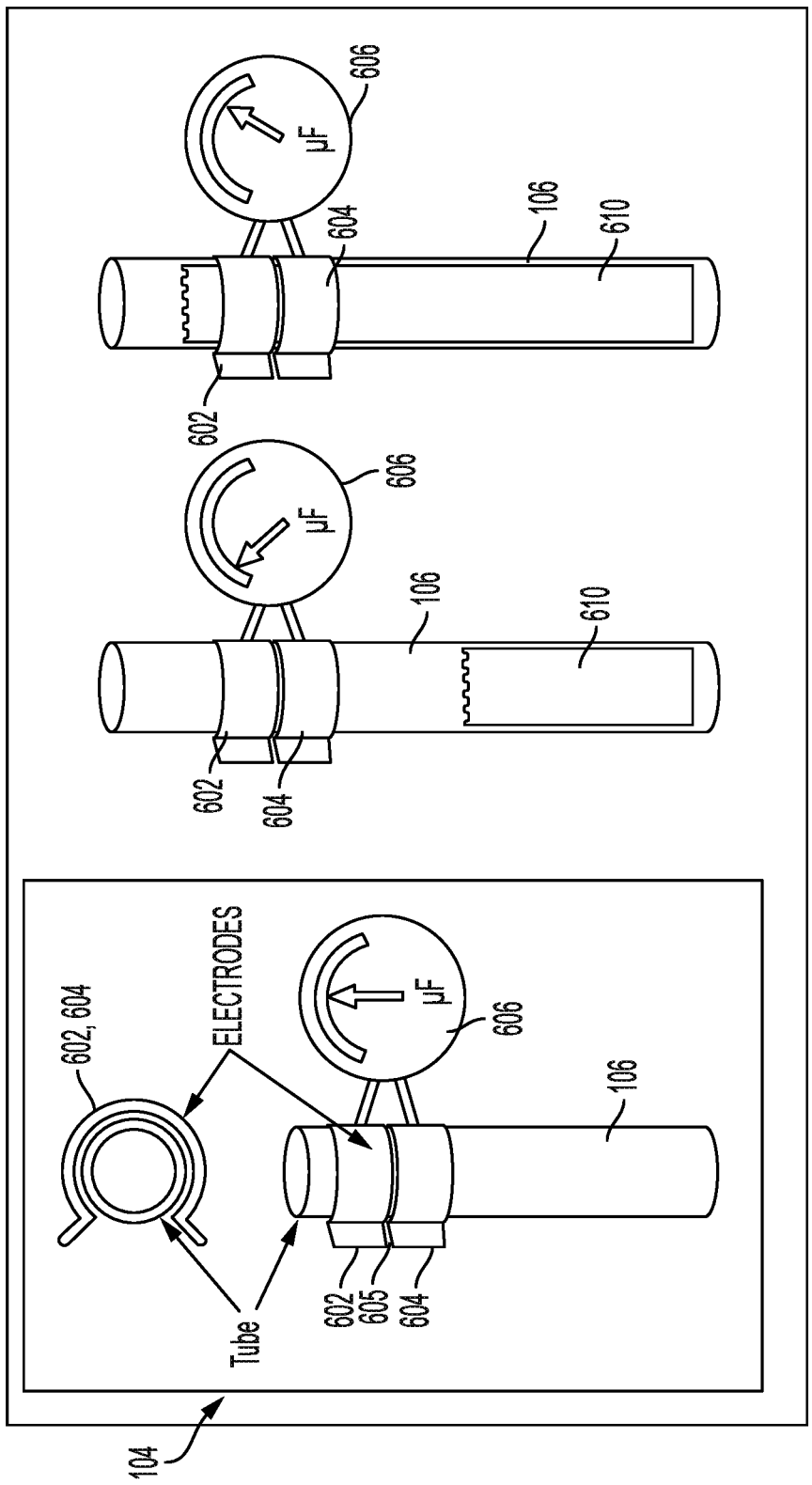
FIG. 6 is an elevation view of electrodes and/or conductive plates of the priming sensor of FIGS. 1 to 5, according to an example embodiment of the present disclosure.

FIG. 6 illustrates electrodes and/or conductive plates of the priming sensor 104 of FIGS. 1 to 5, according to an example embodiment of the present disclosure. In the illustrated example, a first electrode or metallic sheet 602 is provided at a location that is adjacent to a first portion of the tube 106 when the tube is inserted. In addition, a second electrode or metallic sheet 604 is provided at a location that is adjacent to a second portion of the tube 106 when the tube is inserted. The first and second electrodes 602 and 604 may be included or encased within the housing 202 (not shown) of the priming sensor 104. The electrodes 602 and 604 are separated by a gap 605, which may have a width that is between 0.5 millimeters ("mm") and 2 centimeters ("cm"). The electrodes 602 and 604 may have a width that is between 2 mm and 3 cm. The electrodes 602 and 604 are connected to a capacitive sensor 606 (e.g., a capacitance measuring device), which is configured to measure a capacitance between the electrodes 602 and 604. The electrodes 602 and 604 (and other electrodes disclosed herein) may include conductive plates, copper traces on a flexible PC board or cable, metallic plates, carbon filled conductive plastic, metal plated plastic, plastic sprayed with conductive paint, etc. The capacitive sensor 606 (e.g., capacitive sensor 117 of FIG. 1) may be included within the processor 120 or the control unit 115 of FIG. 1 or be provided separately. The capacitive sensor 606 may, for example, be provided on an electronics card or printed circuit board provided with the control unit 115. The processor 120, the capacitive sensor 606, and/or the control unit 115 is powered via a power source of the dialysis machine 102.

As shown in FIG. 6, at a first time, a fluid level 610 in the tube 106 is elevationally below the electrodes 602 and 604. As a result, the capacitance measured at the sensor 606 is primarily based on the dielectric values of the air in the tube 106 and the tube itself. Later, the fluid level 610 rises in the tube 106 during a priming sequence to expel the air. As such, the fluid 610 flows past the electrodes 602 and 604. The presence of the fluid 610 in the portion of the tube 106 that is adjacent to the electrodes 602 and 604 reduces an effective distance between the electrodes 602 and 604, thereby increasing a value of the capacitance measured by the sensor 606. While the fluid 610 does not bridge the gap 605 by physically contacting the electrodes 602 and 604, the placement of the fluid 610 adjacent to the gap 605 is sufficient to change the electric field around and between the electrodes 602 and 604. Detection of a change in electric field is indicative that the fluid level 610 has reached the end of the tube 106 at the electrodes 602 and 604, which is indicative that the pump 110 can stop the priming procedure. Further, the movement of a floating electrode closer to the electrodes 602 and 604 also increases the measured capacitance, which may be used for detecting the presence of the tube 106.

Figure 7:
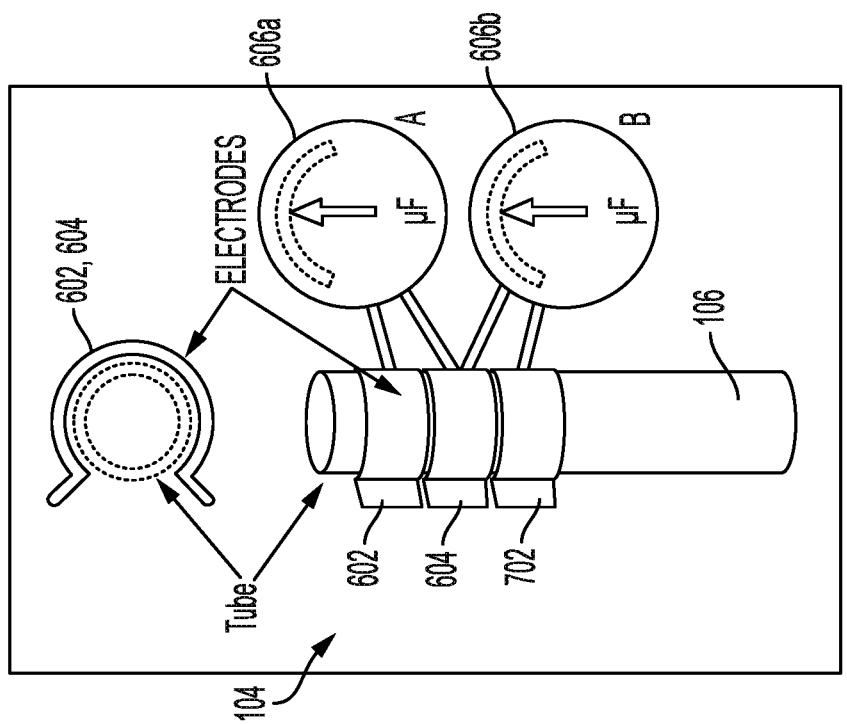
FIG. 7 is an elevation view of the priming sensor of FIGS. 1 to 5, according to another example embodiment of the present disclosure.

FIG. 7 illustrates the priming sensor 104 of FIGS. 1 to 5, according to another example embodiment of the present disclosure. In the illustrated example, the sensor 104 includes three electrodes and/or conductive plates 602, 604, and 702, which are positioned at different elevational heights with respect to the tube 106. The electrodes 602 and 604 are electrically connected to a first capacitive sensor 606a, while the electrodes 604 and 702 are electrically connected to a second capacitive sensor 606b. The capacitive sensors 606a and 606b may be included within the processor 120 (and/or the control unit 115 and communicatively coupled to the processor 120) of FIG. 1 or be provided separately.

The capacitive sensors 606a and 606b collectively provide an indication of fluid level. For example, detection of a fluid by the second sensor 606b but not the first sensor 606a is indicative that the fluid level has reached a height in the tube 106 greater than the end of the electrode 604 but less than a lower end of the electrode 602. Detection of the fluid level at such a level may cause the processor 120 of the control unit 115 to decrease a pumping speed of the pump 110. Detection of the fluid by the first sensor 606a is indicative that the fluid has reached at least a height in the tube 106 that is adjacent to the electrode 602. Detection of the fluid level at this elevation may cause the processor 120 of the control unit 115 to stop the priming sequence using the pump 110. If neither of the sensors 606a and 606b detects an increase in capacitance, the processor 120 of the control unit 115 may be configured to cause the pump 110 to operate at normal priming speed to prime the tube 106 with fluid.

Figure 8:
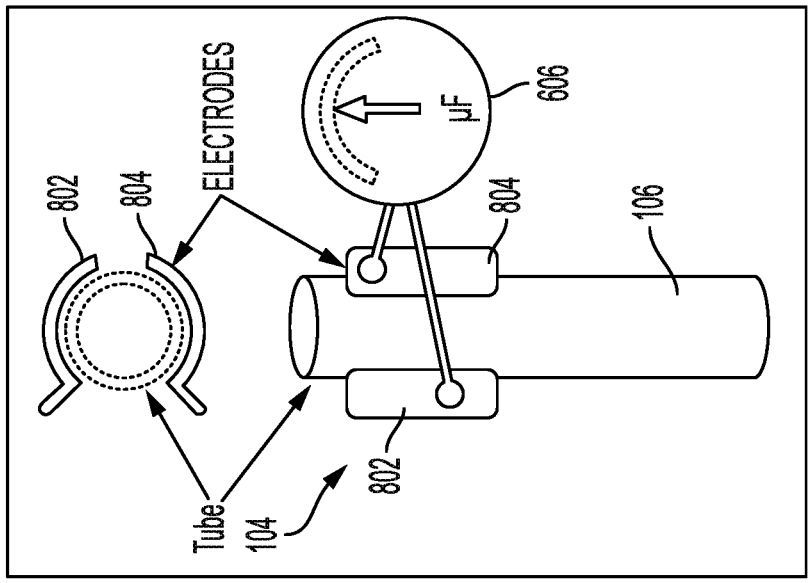
FIG. 8 is an elevation view of the priming sensor of FIGS. 1 to 5, according to a further example embodiment of the present disclosure.

FIG. 8 illustrates the priming sensor 104 of FIGS. 1 to 5, according to further example embodiment of the present disclosure. In this example, a first electrode or conductive plate 802 is placed on a first side of the tube 106, while a second electrode or conductive plate 804 is placed on a second side of the tube 106. As illustrated, the first electrode 802 is placed on a first side of the recessed section 302 of the housing 202, which is opposite to a second side of the recessed section 302, which contains the second electrode 804.

The electrodes 802 and 804 are electrically connected to a capacitive sensor 606, which is configured to measure a capacitance between the electrodes. The measured capacitance includes values that are indicative of the capacitance. As shown in FIG. 8, when a fluid is not present, the capacitive sensor 606 measures a capacitance of the tube 106 and air within the tube. When the fluid displaces the air, the capacitive sensor 606 measures a capacitance of the tube 106 and the fluid. The capacitance of the tube 106 itself is normalized or otherwise neglected when detecting a change in capacitance due to the transition from air to fluid within the tube 106.

In some embodiments, a fluid level may be determined based on the measured capacitance. For instance, the capacitance may be lower when the fluid level in the tube 106 is only aligned with a bottom portion or end of the electrodes 802 and 804 and greater when the fluid level is aligned with the top portion or end of the electrodes. The value of the capacitive may be correlated via a table or other data structure to a height in the tube 106. This value may be used by the processor 120 of the control unit 115 for gradually decreasing a speed of the pump 110 as the fluid level approaches a top (open) end of the tube 106.

Figure 9:
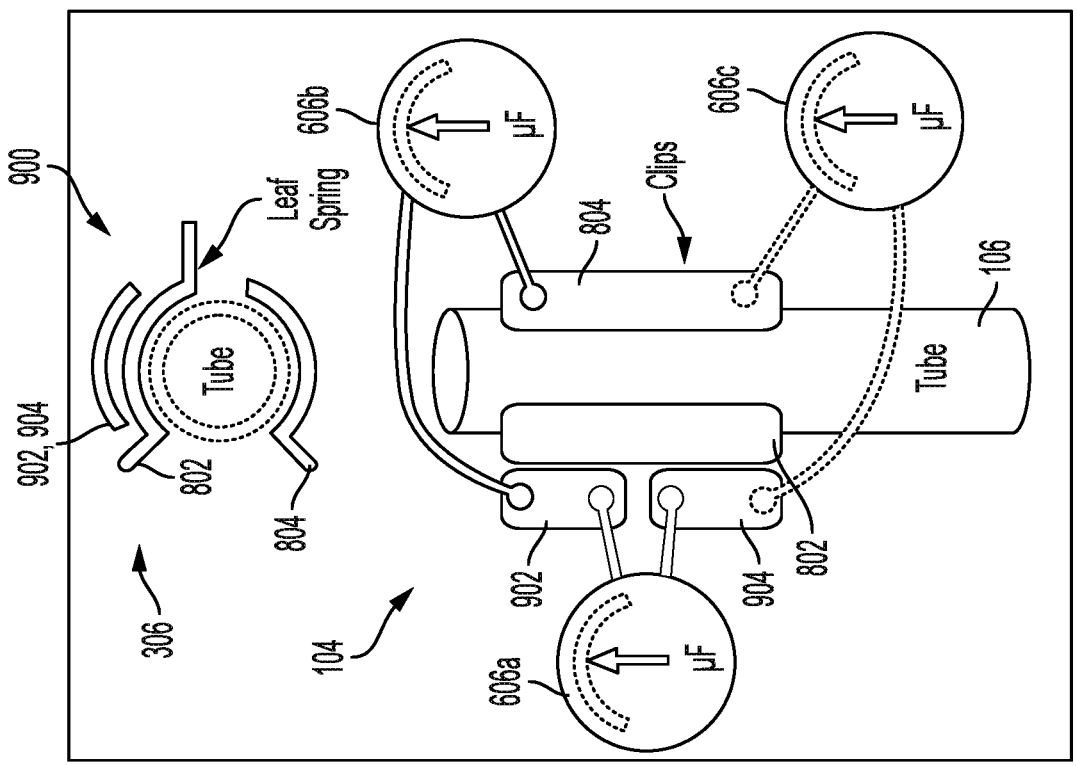
FIG. 9 is an elevation view of the priming sensor of FIGS. 1 to 5, according to yet another example embodiment of the present disclosure.

FIG. 9 illustrates the priming sensor 104 of FIGS. 1 to 5, according to yet another example embodiment of the present disclosure. Similar to the example of FIG. 8, the electrodes 802 and 804 are positioned opposite of one another. However, as shown in a plan view 900, the electrode 802 is included within the retaining clip 306. As such, the electrode 802 is moveable relative to the electrodes 804, 902 and 904, which are held stationary via the housing 202. An end or base of the electrode 802 is connected to a base or middle portion of the recessed section 302. The retaining clip 306 is configured to pivot or bend at the end of the electrode 802, thereby enabling the clip 306 to be moved between opened and closed positions. Further, the biased nature of the electrode 802 to return to its initial position within the recessed section 302 causes the retaining clip 306 to provide a spring force on the tube 106 when inserted into the priming sensor 104. It should be appreciated that in some examples, the electrode 802 is not electrically connected to other portions of the priming sensor 104, thereby enabling it to float electrically.

The example priming sensor 104 of FIG. 9 also includes the electrodes 902 and 904. As shown in plan view 900, the electrodes 902 and 904 are provided on a side of the recessed section 302, which is opposite to that of the electrode 804. The electrodes 902 and 904 are stationary and are configured to at least partially encircle the tube 106.

Similar to the example discussed in connection with FIG. 6, the electrodes 902 and 904 are positioned at different elevational heights relative to each other. In the illustrated example, the electrode 902 is placed at a greater height or elevation than is the electrode 904, providing a gap therebetween. The electrodes 902 and 904 may have the same width or different widths.

The electrodes 902 and 904 are electrically connected to a first capacitive sensor 606*a*, which is configured to measure a capacitance value between the electrodes 902 and 904. In the illustrated example, the capacitive sensor 606*a* is configured to detect a change between the no-tube state and the dry tube state. In the illustrated example, the capacitive sensor 606*a* is configured to detect a capacitance change as a result of the electrode 802 being moved closer to the electrodes 902 and 904 when, for example, the tube 106 is inserted within the priming sensor 104. Movement of the electrode 802 towards the electrodes 902 and 904 causes the measured capacitance to increase, which is indicative that the tube 106 has been inserted within the priming sensor 106.

In some embodiments, the capacitive sensor 606*a* may also be used to detect a capacitance change when a dialysis fluid level rises to bridge the gap between the electrodes 902 and 904. As such, the capacitive sensor 606*a* may be configured to additionally detect transitions between a dry tube and a wet tube. Outputs from the sensor 606*a* are used by the processor 120 of the control unit 115 to determine the dry tube state and the wet tube state, as discussed in connection with FIG. 6.

As shown in FIG. 9, the electrodes 804 and 902 are electrically connected to a second capacitive sensor 606*b*. In the illustrated example, the capacitive sensor 606*b* is configured to detect a capacitance increase as a result of the fluid level rising between the electrodes 804 and 902. The capacitive sensor 606*b* is used to detect transitions between a dry tube state and a wet tube state.

Similarly, electrodes 804 and 904 are electrically connected to a third capacitive sensor 606*c*. The third capacitive sensor 606*c* is configured to detect a capacitance increase as a result of fluid rising between the electrodes 804 and 904. The capacitive sensor 606*c* is used to detect transitions between a dry tube state and a wet tube state.

In some embodiments, the outputs (or values indicative of measured capacitances) of the capacitive sensors 606*b* and 606*c* are added together or otherwise combined by the processor 120 of the control unit 115 for detecting the dry tube state and the wet tube state. In some embodiments, the processor 120 may compare the outputs from the capacitive sensors 606*b* and 606*c* for determining a fluid level in the tube 106. For example, a significant difference between the measured capacitances is indicative that the fluid level in the tube 106 has not yet reached a height of the electrode 902 but has reached the height of the electrode 904. Detection of the fluid at this level may cause the processor 120 to reduce a pumping speed of the pump 110.

Figures 10, 11:
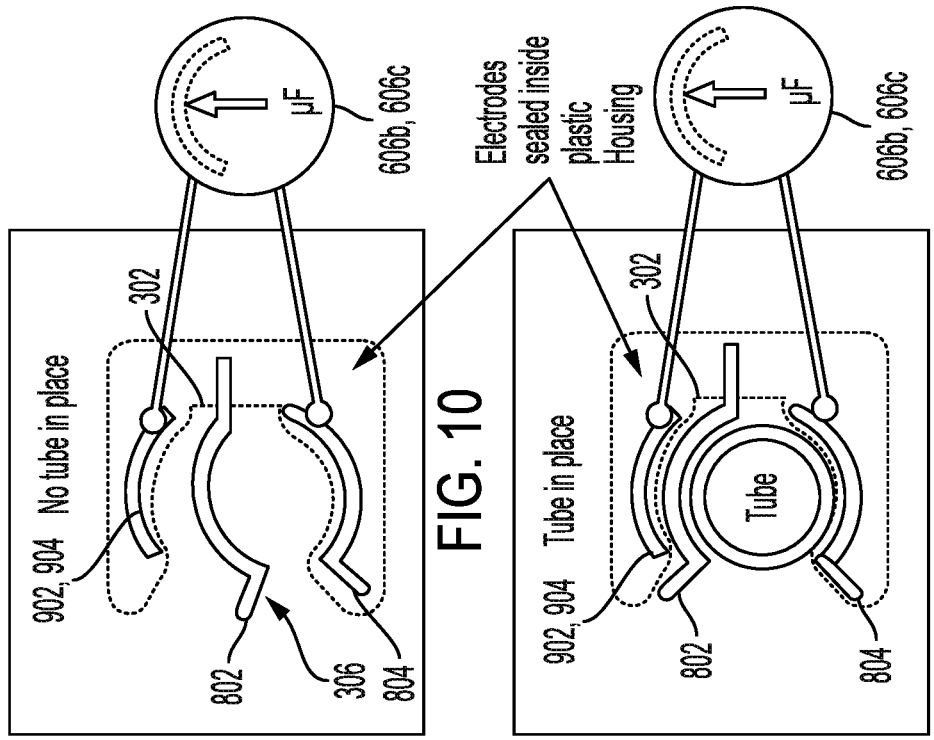
FIG. 10 is a top view of a retaining clip and an electrode of the priming sensor of FIG. 9 in a closed and resting position when a tube is not inserted therein, according to an example embodiment of the present disclosure.
FIG. 11 is a top view of the retaining clip and the electrode of FIG. 10 when a tube is inserted therein, according to an example embodiment of the present disclosure.

FIGS. 10 and 11 show a plan view of the priming sensor 104, according to an example embodiment of the present disclosure. FIG. 10 shows the retaining clip 306 and the electrode 802 in a closed and resting position when the tube 106 is not inserted into the priming sensor 104. FIG. 10 also shows a base or end of the electrode 802 connected to a middle-section or base of the recessed section 302. FIG. 11 shows the electrode 802, including the retaining clip 306, bent, pivoted, or otherwise moved towards the electrode 902 as a result of the tube 106 being inserted into the priming sensor 104. The retaining clip 306 and/or the electrode 802 is configured such that the tube 106 can only be inserted into a desired alignment. The retaining clip 306 and/or the electrode 802 may include, for example, a front end that is angled for receiving and directing the tube 106 to a middle of the recessed section 302. As discussed above in connection with FIG. 9, placement of the tube 106 in the recessed section 302 causes the electrode 802 to move towards electrodes 902 and 904, thereby increasing the measured capacitance.

Figure 12:
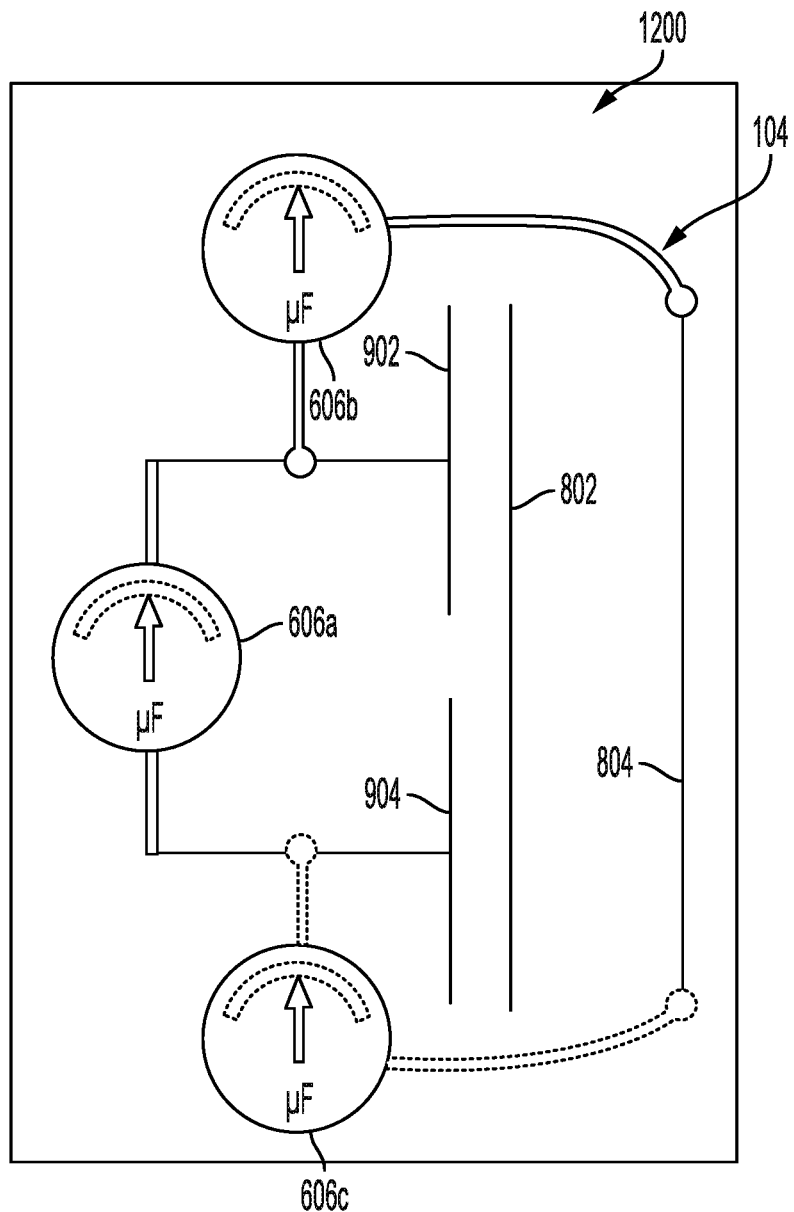
FIG. 12 is a schematic view of a circuit diagram showing the capacitors formed by the electrodes of FIGS. 9 to 11, according to an example embodiment of the present disclosure.

FIG. 12 shows a circuit diagram 1200 for one embodiment of the capacitors formed by the electrodes 802, 804, 902, and 904 of FIGS. 9 to 11, according to an example embodiment of the present disclosure. As shown, the electrodes 804 and 902 form a first capacitor while electrodes 804 and 904 form a second, parallel capacitor. The capacitance of the first and second capacitors is based on a position of the electrode 802 relative to the electrodes 902 and 904. The electrodes 902 and 904, as discussed herein, form a third capacitor.

Processor Embodiment

Figure 13:
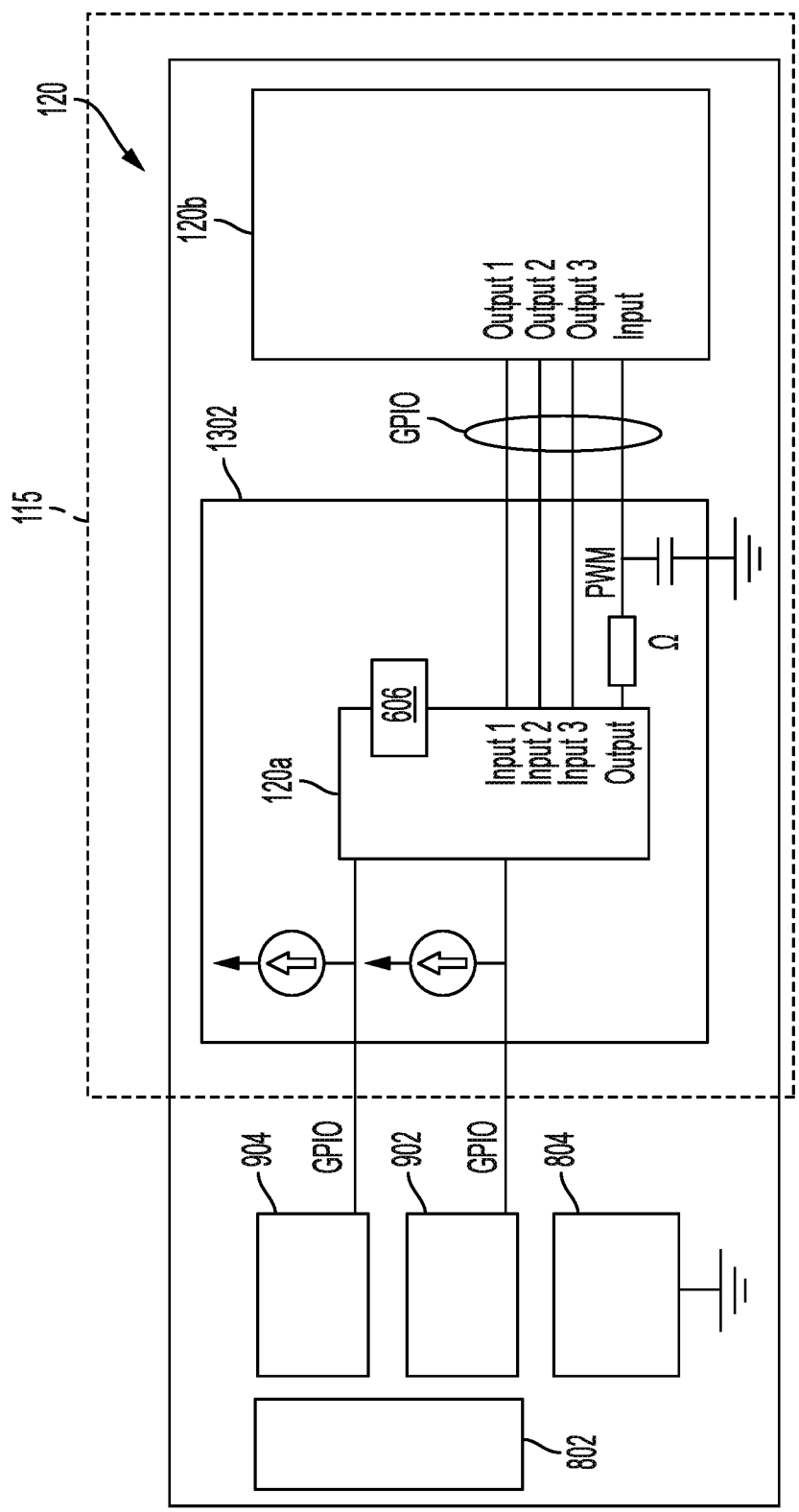
FIG. 13 is a schematic view of a diagram of a processor or control unit of the dialysis machine illustrated in FIG. 1, according to an example embodiment of the present disclosure.

The example processor 120 of the control unit 115 of FIG. 1 is configured, in part, to determine a tube state based on capacitance measured by one or more capacitive sensors. FIG. 13 shows the processor 120 of FIG. 1, according to an example embodiment of the present disclosure. The processor 120 includes a first processing device 120*a* and a second processing device 120*b*. The first processing device 120*a* is provided on a circuit board or processor board 1302. In the example, the first processing device 120*a* is electrically connected to the electrodes 902 and 904 via General Purpose Input Output ("GPIO") traces or lines. In some instances, current sources (or one or more power sources) may be connected to the GPIO lines to provide current to enable the capacitance measurements. The current sources may provide, for example, a current of 10 nA, 100 nA, 250 nA, 500 nA, 1000 nA, etc.

Also shown in FIG. 13, the electrode 804 is electrically connected to ground. The ground may be shared in common with a ground for the processing device 120*a*, such that the processing device 120*a* is electrically connected to the electrode 804 via ground. In other embodiments, the electrode 804 is instead connected to the processing device 120*a* via a third GPIO line or trace. Further, as discussed above, the electrode 802 is not electrically connected to the processing device 120*a* and is therefore permitted to electrically float.

The processing device 120*a* includes and/or operates with the capacitive sensors 606*a*, 606*b*, and 606*c*, which measure capacitance via the GPIO lines. For example, the sensor 606*a* operates with the processing device 120*a* to measure a capacitance between the electrodes 902 and 904 by determining a capacitance between the GPIO lines. The sensor 606*b* operates with the processing device 120*a* to measure a capacitance between the electrodes 804 and 902 by determining a capacitance between the second GPIO line and ground. The sensor 606*c* operates with the processing device 120*a* to measure a capacitance between the electrodes 804 and 904 by determining a capacitance between the first GPIO line and ground.

Figure 14:
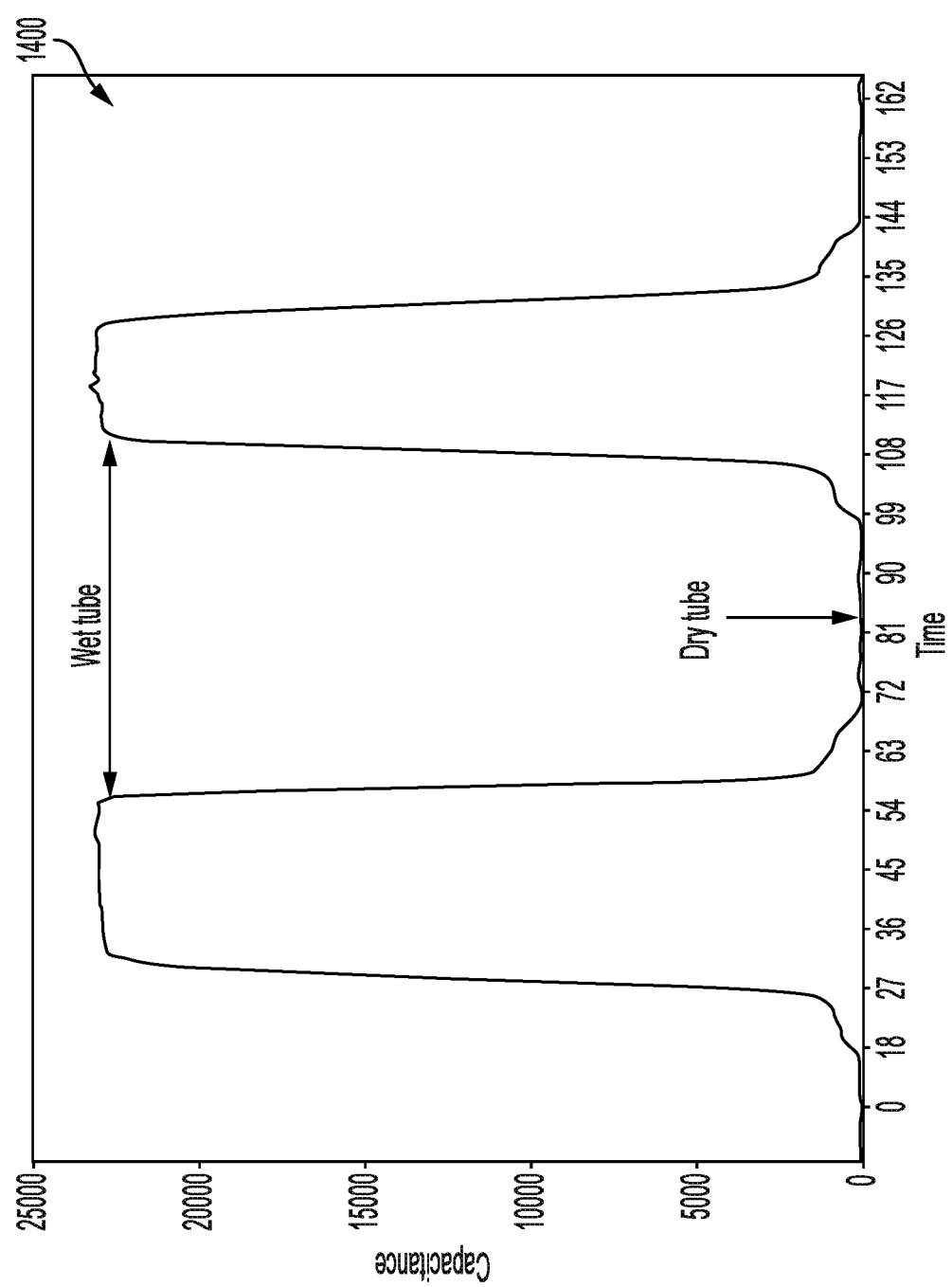
FIG. 14 is a graph of capacitance measured over a time period by the priming sensor of FIGS. 9 to 13, according to an example embodiment of the present disclosure.

FIG. 14 shows a graph 1400 illustrating example capacitance values measured by the sensors 606*a*, 606*b*, and 606*c* of FIGS. 9 to 13 over a time period, according to an example embodiment of the present disclosure. The graph 1400 shows units of normalized capacitance over 16.2 seconds. The capacitance may be normalized from measured values having an order of magnitude of femtofarads ("fF") or picofarads ("pF"). The graph 1400 shows a transition between a dry tube state and a wet tube state, as measured by the capacitive sensors 606*b* and 606*c*. As shown, the normalized capacitance changes by about 23000 units within a few tenths of a second as the liquid level in the tube 106 reaches the electrodes 804, 902, and 904. The magnitude of the capacitance is substantially level or consistent after the wet state is reached. When the liquid level is reduced, the capacitance quickly falls off to return to a normalized value of '0,' thereby producing a square-shaped waveform. As can be appreciated, the significant capacitance difference between the states provides a robust signal-to-noise ratio that is greater than 1000:1, providing for accurate tube state detection. It should be appreciated that the graph 1400 is similar in magnitude and shape for transitions between the no-tube state and the dry tube state.

Returning to FIG. 13, after measuring a capacitance, the first processing device 120*a* is configured to transmit one or more signals or messages that are indicative of the capacitance to the second processing device 120*b*. In the example, the second processing device 120*b* transmits input instructions or signals via separate input lines. The first processing device 120*a* may use the input instructions or signals for sampling or performing capacitance measurements. For example, a first input from the second processing device 120*b* may instruct the first processing device 120*a* to measure a capacitance of the first capacitive sensor 606*a*, while the second input may instruct the first processing device 120*a* to measure a capacitance of the second capacitive sensor 606*b*, while the third input may instruct the first processing device 120*a* to measure a capacitance of the third capacitive sensor 606*c*.

In some embodiments, the first processing device 120*a* is configured to determine a tube state based on the measured capacitance values determined via the GPIO lines. The first processing device 120*a* transmits an indication of each tube state or an indication of a tube state change to the second processing device 120*b* via, for example, a pulse-width modulated ("PWM") signal or an analog signal produced by a digital-to-analog converter ("DAC") within the first processing device 120*a*. In alternative examples, the PWM signal may be replaced by a digital signal or instruction that is indicative of the tube state.

In some embodiments, the first processing device 120*a* is configured to sample or perform multiple capacitance measurements before conclusively determining that a tube state has changed. For example, if a threshold number of measurements (e.g., one, two, three, five, ten, etc.) are indicative of the same tube state within a threshold time period (e.g., 10 ms, 100 ms, 250 ms, 500, ms, 1 second, 2 seconds, 5 seconds, etc.), the first processing device 120*a* determines the tube state has in fact changed. If at least one of the thresholds is not met, the processing device 120*a* refrains from determining a tube state change. The above-situation may occur when electrical interference is present due to an operator's hand or electronic device.

Alternatively, the first processing device 120*a* transmits an indication of the measured capacitances to the second processing device 120*b* via a PWM signal or an analog signal produced by the DAC within the first processing device 120*a*. A pulse width may correspond to a value of the measured capacitance. In alternative examples, the PWM signal may be replaced by a digital signal or instruction that is indicative of measured capacitance. After receiving capacitance values from the first processing device 120*a*, the second processing device 120*b* is configured to determine a tube state. In some examples, the processing device 120*b* may sample or perform multiple capacitance measurements (by transmitting messages via the separate input lines to the first processing device 120*a*) for determining tube state. If a threshold number of measurements (e.g., one, two, three, five, ten, etc.) are indicative of the same tube state within a threshold time period (e.g., 10 ms, 100 ms, 250 ms, 500, ms, 1 second, 2 seconds, 5 seconds, etc.), the second processing device 120*b* determines the tube state has in fact changed. If at least one of the thresholds is not met, the processing device 120*b* refrains from determining a tube state change.

Figure 15:
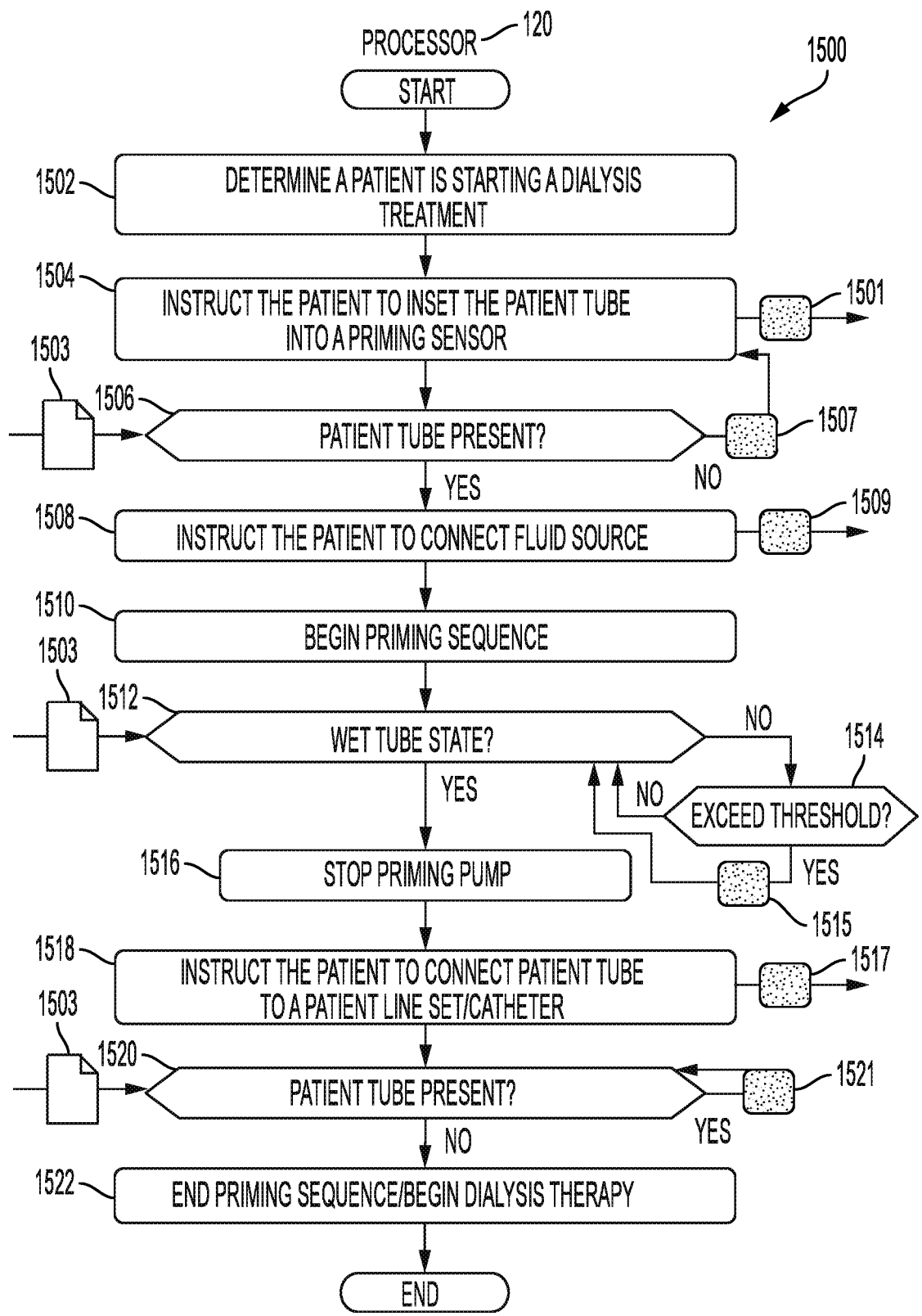
FIG. 15 is a process flow diagram for determining a tube state of a patient tube, according to an example embodiment of the present disclosure.
Figure 17:
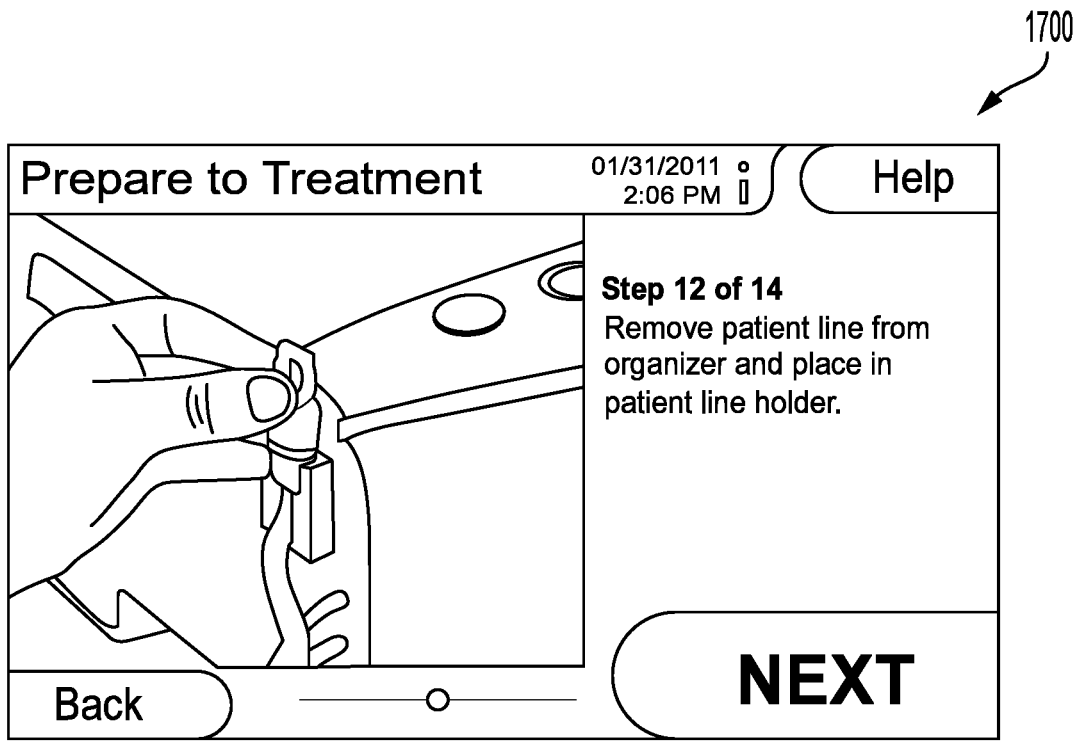
FIGS. 17 to 23 are graphical screens that may be displayed by a dialysis machine to assist a patient in performing a priming procedure in preparation of a dialysis therapy, according to example embodiments of the present disclosure.

FIG. 15 illustrates an example procedure 1500 for determining a tube state of the patient tube 106 of FIG. 1, according to an example embodiment of the present disclosure. The example processor 120 of the control unit 115 is configured to execute or operate the procedure 1500 shown in FIG. 15. To begin, the example processor 120 receives an indication or determines that a patient is to start a dialysis treatment (block 1502). The example processor 120 may receive an input via the user interface 124 that a patient has selected to begin a treatment. Alternatively, the processor 120 may determine via an electronically stored schedule that a patient is to undergo a dialysis treatment. To prepare for the treatment, the example processor 120 operates a setup routine in one embodiment, which may include connecting tubes to appropriate containers and performing a priming procedure. When it is time to prime the patient tube 106, the example processor 120 transmits a message 1501 for display via the user interface 124 that the patient is to inset the patient tube 106 into the priming sensor 104 (block 1504). FIG. 17 illustrates an example screen layout 1700 that may be displayed by the user interface 124 based on the message 1501. The screen layout 1700 includes text and an illustration regarding how the patient tube 106 is to be placed within the priming sensor 104.

Figure 18:
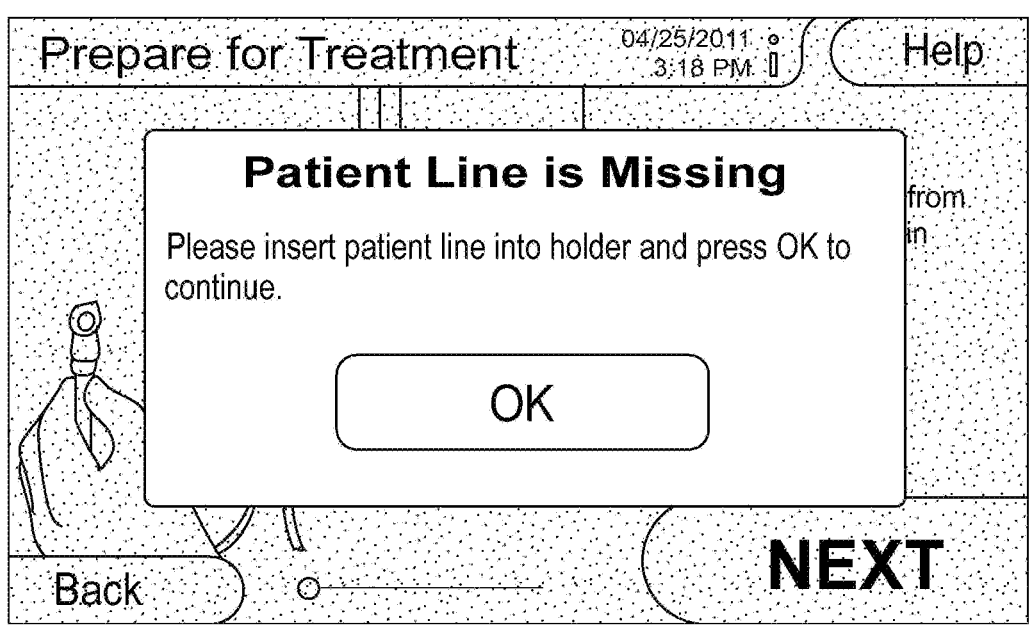

To determine if the patient correctly inserted the tube 106 into the priming sensor 104, the example processor 120 is configured to perform one or more capacitive measurements to determine a tube state (block 1506). For each capacitive measurement performed, the processor 120 receives sampled output data 1503 from one or more of the capacitive sensors 606, which is processed to determine a tube state, as discussed above in connection with FIGS. 9 to 14. If the no-tube state is detected, the processor 120 is configured to transmit one or more messages 1507 indicative that the patient tube 106 is missing. FIG. 18 illustrates a diagram of a screen layout 1800 that may be displayed by the user interface 124 based on the message 1507. The screen layout 1800 includes a pop-up window alerting the patient that the patient tube 106 has not been inserted.

Figure 19:
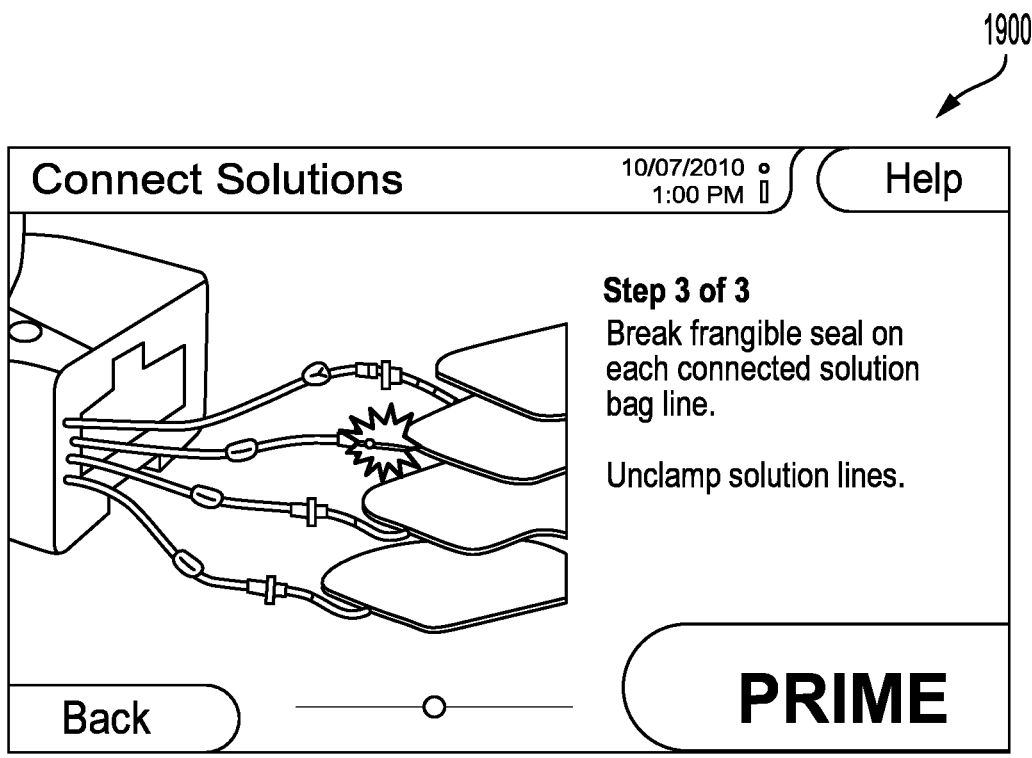
Figure 20:
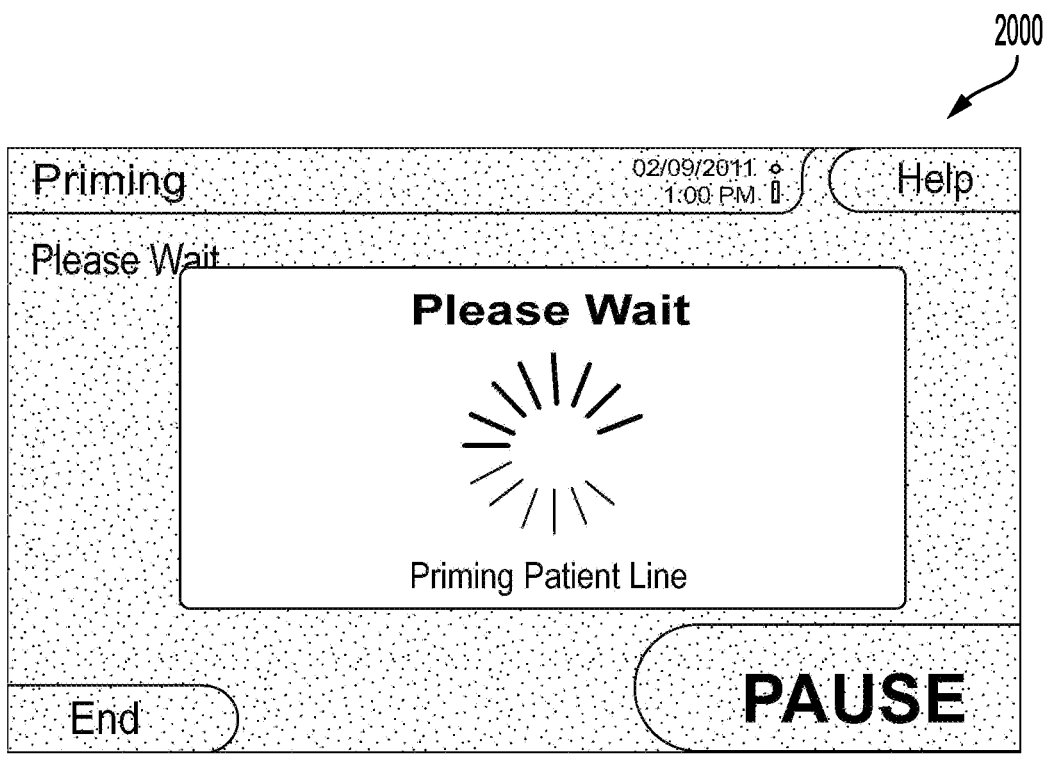

Returning to FIG. 15, if a dry tube state is detected, the example processor 120 transmits one or more messages 1509 indicative that the patient is to connect a tube to a fluid source (block 1508). In other embodiments, the message 1509 may instruct a patient to begin a priming sequence. FIG. 19 shows a diagram of a screen layout 1900 that may be displayed by the user interface 124 based on the message 1509. The screen layout 1900 includes text and images regarding how a fluid source is to be connected to one or more source tubes of a dialysis machine. After the patient has connected the tubes, the patient may select the priming button shown in the screen layout 1900. Selection of the priming button provides an indication for the processor 120 to begin a priming sequence (block 1510). The priming sequence includes causing at least one pump 110 to move dialysis fluid from at least one source container 112 to the patient tube 106. During this sequence, the processor 120 receives sampled output data 1503 from performing multiple capacitance measurements or sampling of capacitance measurements that are conducted by the capacitive sensors 606 (block 1512). In addition, during this sequence, the processor 120 may cause a screen layout 2000 shown in FIG. 20 to be displayed on the user interface 124, which is indicative that a priming sequence is being run.

Figure 21:
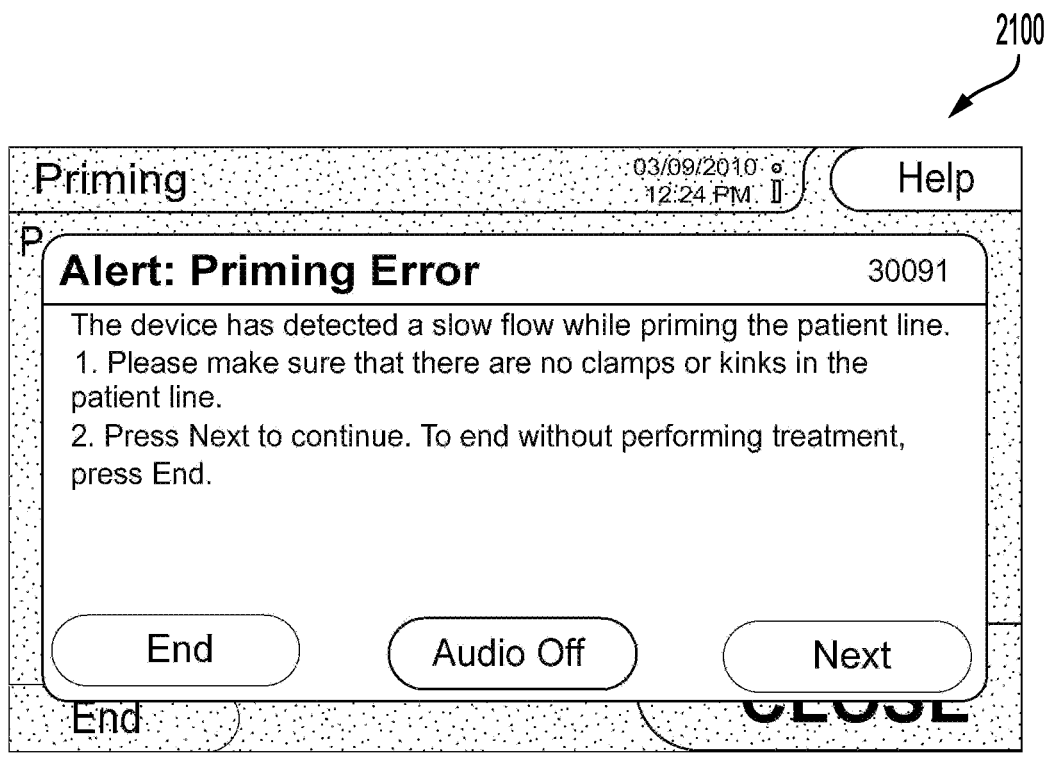

For each detection of a dry tube state, the processor 120 may increment a threshold counter and determine whether the counter exceeds a threshold (block 1514). If the threshold is not exceeded within a specified time period (e.g., 250 ms, 500 ms, 1 second, 3 seconds, 10 seconds, 20 seconds, 40 seconds, etc.), the patient tube 106 is not able to prime within an expected time period and may have an occlusion, leak, constriction, or other condition that is preventing dialysis fluid from filling the tube. In an attempt to correct the situation, the processor 120 is configured to transmit one or more messages 1515, which causes screen layout 2100 of FIG. 21 to be displayed. In addition, an alarm may be activated. The screen layout 2100 includes text indicative of the priming error and instructions for the patient to check the tubes from the source fluid and the patient tube 106. After a patient has identified and corrected the issue with the tubes, the patient may select the next button to re-start the priming sequence.

Figure 22:
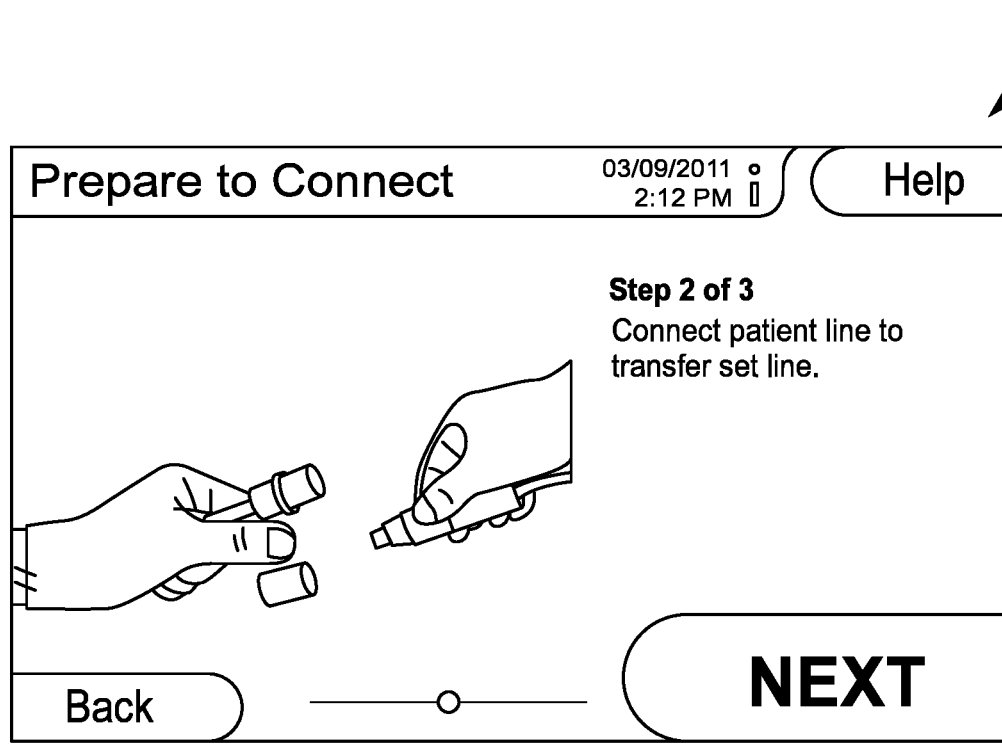

Returning to block 1512, if a wet tube state is detected within a threshold time, the example processor 120 may be configured to stop the pump 110 from priming (block 1516). In some embodiments, the example processor 120 is configured to confirm that the prime has been correctly performed. The example processor 120 may also transmit one or more messages 1517 with information instructing the patient to connect the patient tube 106 to a patient line set and/or catheter to begin treatment (block 1518). FIG. 22 illustrates a diagram of a screen layout 2200 that may be displayed by the user interface 124 based on the message 1517. The screen layout 2200 includes text and an image providing a patient information regarding how to connect the patient tube 106 to a line set or catheter.

Figure 23:
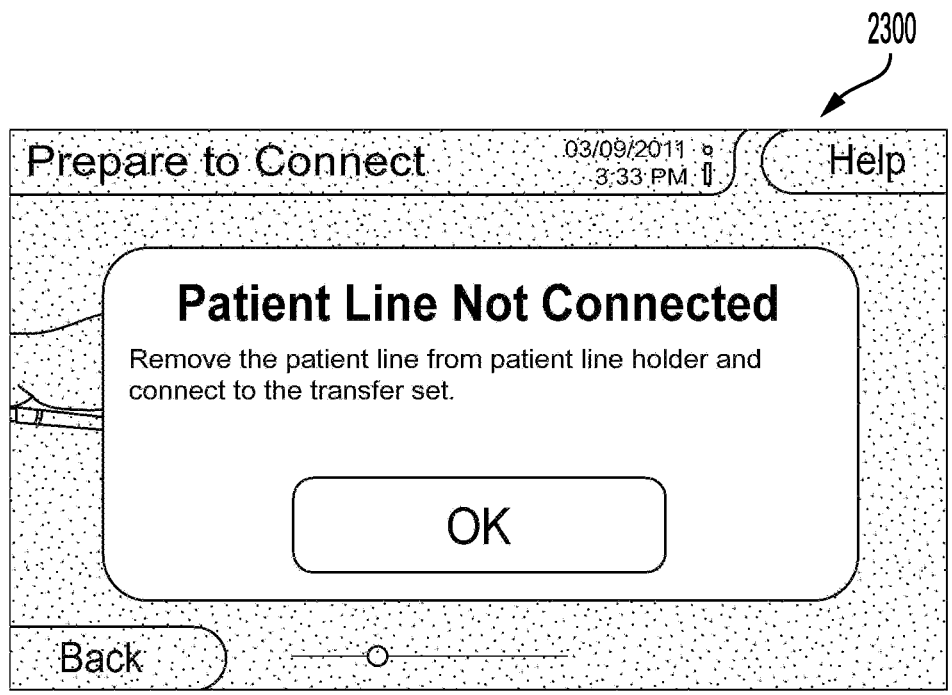

Returning to FIG. 15, the example processor 120 is configured to use the priming sensor 104 to determine if the patient tube 106 is still present in the sensor (block 1520). The processor 120 receives one or more sets of sampled output data 1503 to determine if the tube is still in the priming sensor 104. If the tube is still present, the processor 120 transmits one or more messages 1521 indicative that the patient is to remove the tube from the priming sensor 104. FIG. 23 illustrates a diagram of a screen layout 2300 that may be displayed by the user interface 124 based on the message 1521. The screen layout 2300 includes a pop-up window providing a warning that that the patient tube has not been removed from the priming sensor for connection to a line set or catheter. If the patient tube 106 is no longer detected, the example processor 120 is configured to end the priming sequence and/or enable the dialysis therapy to begin.

Figure 16:
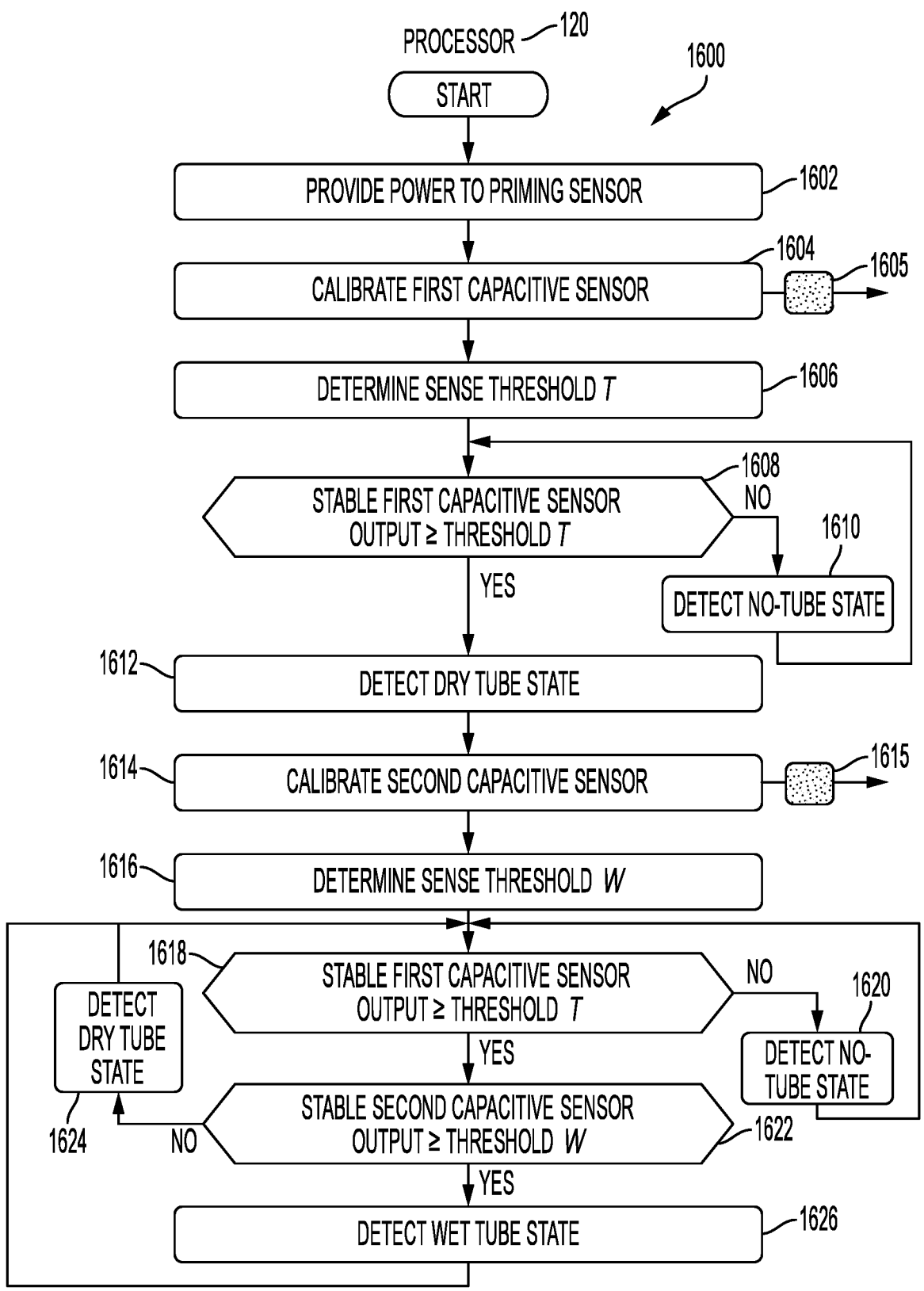
FIG. 16 is a process flow diagram for determining a tube state of a patient tube, according to an example embodiment of the present disclosure.

FIG. 16 shows a diagram of an example procedure 1600 configured to determine a tube state of the patient tube 106 for a priming sequence, according to an example embodiment of the present disclosure. The example procedure 1600 may be executed or performed by the processor 120 of FIG. 1. Further, the processor 1600 may operate according to one or more instructions stored in the memory 122, which when executed by the processor 120, cause the processor 120 to perform the described operations. In some embodiments, the processor 120 may additionally normalize the measured capacitance values.

The example procedure 1600 begins when the processor 120 performs a priming sequence and provides power to the priming sensor 104 (block 1602). The example processor 120 calibrates the capacitive sensor 606*a* of FIG. 9 (block 1604). The processor 120 may calibrate the sensor 606*a* by determining steady state measured capacitance. The processor 120 may determine an average of the measured capacitance values for calculating a baseline value 1605. After calibration, the processor 120 stores the determined baseline capacitance value 1605 to the memory 122.

The processor 120 then computes a sense threshold T (block 1606). The threshold T is a capacitance value that is greater than the baseline value 1605. In some embodiments, the processor 120 determines the threshold T as being 2×, 3×, 4×, 5×, 7×, 10×, 15×, 20×, etc., greater than the baseline value 1605. In other embodiments, the processor 120 determines the threshold T as being a specified number of fF or pF above the baseline value. Measured capacitance values below the threshold T are determined by the processor 120 to correspond to a no-tube state, while measured capacitance values above the threshold T are determined by the processor 120 to correspond to a dry tube state. For instance, the processor 120 compares measured capacitance values from the sensor 606*a* to the threshold T (block 1608). If the measured capacitance values are less than the threshold T, the processor 120 determines the measured values correspond to the no-tube state (block 1610). In some instances, the processor 120 may also update a counter, where no detections of a no-tube state within a specified time period may cause the processor 120 to output an error message or activate an alert. The processor 120 then continues to compare (or sample) subsequent measured capacitance values from the capacitive sensor 606a to the threshold T.

Returning to block 1608, if the measured capacitance values are greater than or equal to threshold T, the processor 120 determines the measured value corresponds to a dry tube state (block 1612). In some instances, the processor 120 may only determine a dry tube state if a threshold number of dry state tube detections are made within a specified time period (e.g., two, five, or ten detections within 100 ms, 250 ms, 500 ms, 1 s, 2 s, 5 s, etc.).

The processor 120 next calibrates the capacitive sensor 606b and/or 606c of FIG. 9 (block 1614). In some embodiments, the processor 120 calibrates the capacitive sensors 606a, 606b, and 606c at substantially the same time or at the same time within the example procedure 1600. The processor 120 may calibrate the sensor 606b and/or 606c by determining steady state measured capacitances. The processor 120 may determine an average of the measured capacitance values for calculating a baseline value 1615. After calibration, the processor 120 stores the determined baseline capacitance value 1615 to the memory 122.

The processor 120 of the control unit 115 then computes a sense threshold W (block 1616). The threshold W is a capacitance value that is greater than the baseline value 1615. In some embodiments, the processor 120 determines the threshold W as being 2×, 3×, 4×, 5×, 7×, 10×, 15×, 20×, etc., greater than the baseline value 1615. In other embodiments, the processor 120 determines the threshold W as being a specified number of fF or pF above the baseline value. Measured capacitance values below the threshold W are determined by the processor 120 to correspond to a dry tube state, while measured capacitance values above the threshold W are determined by the processor 120 to correspond to a wet tube state.

After the threshold W is determined, the processor 120 is ready to determine a tube state. As shown in FIG. 16, the processor 120 is configured to compare measured capacitance values from the sensor 606a to the threshold T (block 1618). If the measured capacitance values are less than the threshold T, the processor 120 determines the measured values correspond to the no-tube state (block 1620). The processor 120 continues this loop until the measured capacitance values are greater than or equal to the threshold T. The processor 120 then compares measured capacitance values from the sensor 606b and/or 606c to the threshold W (block 1622). In some instances, the processor 120 may combine the measured capacitance values from the sensors 606b and 606c for the baseline value 1615, the threshold W, and state detection. If the measured capacitance values are less than the threshold W, the processor 120 determines the measured values correspond to the dry tube state (block 1624). The processor 120 may return to block 1618 and determine if the tube is still present in the priming sensor 104 or determine if the tube has been removed. In some instances, the processor 120 may also update a counter, where zero detections of a wet tube state within a specified time period may cause the processor 120 to output an error message or activate an alert indicative of an occlusion, tube leak, etc. The processor 120 then continues to compare (or sample) subsequent measured capacitance values from the capacitive sensors 606b and/or 606c to the threshold W.

Returning to block 1622, if the measured capacitance values are greater than or equal to threshold W, the processor 120 determines the measured value corresponds to a wet tube state (block 1626). In some instances, the processor 120 of the control unit 115 may only determine a wet tube state if a threshold number of wet state tube detections are made within a specified time period (e.g., two, five, or ten detections within 100 ms, 250 ms, 500 ms, 1 s, 2 s, 5 s, etc.). After detecting a wet tube state, the example processor 120 may end a priming sequence, thereby ending the example procedure 1600. Alternatively, the processor 120 returns to block 1618 and determines if the tube has been removed from the priming sensor 104.

Addition Priming Sensor Embodiment

Figure 24:
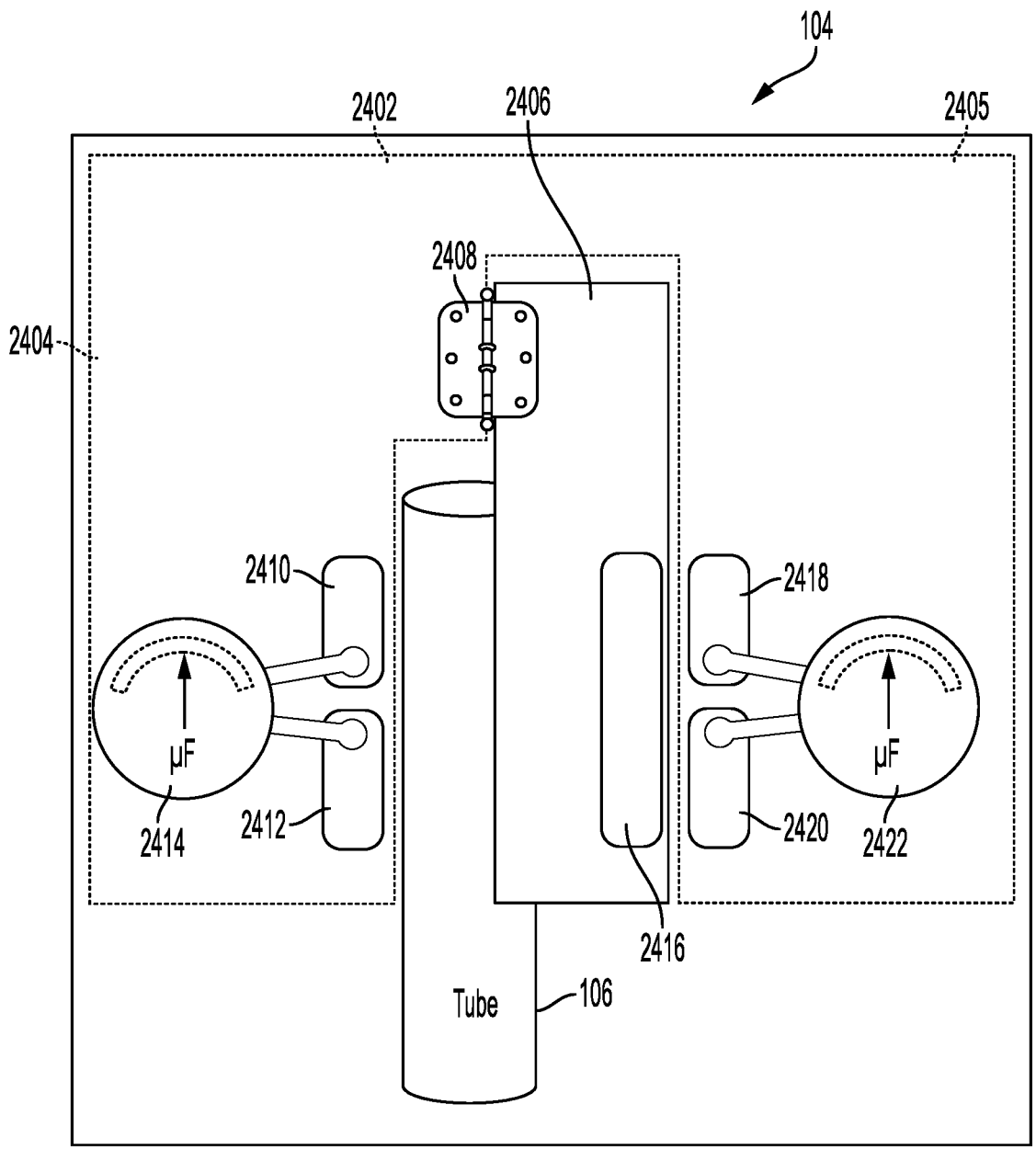

FIG. 24 shows a diagram of the priming sensor 104 of FIG. 1, according to another example embodiment of the present disclosure. In the illustrated example, the priming sensor 104 includes a housing 2402 that is provided in a u-shape. The housing 2402 includes a first arm or side 2404 and a second arm or side 2406. The housing 2402 also includes a joint or hinge 2408 that enables the second arm or side 2406 to rotate or pivot with respect to the first arm or side 2404 or a base 2405 of the u-shaped housing 2402 (e.g., a third side).

In the illustrated example, the first arm or side 2404 includes conductive plates 2410 and 2412. The plates may be solid and placed adjacent to the other. Alternatively, the plates may be interleaved in a comb or finger configuration to provide a relatively broad sensitive area. The conductive plate 2410 is provided at a first height relative to the patient tube 106 and the conductive plate 2412 is provided at a second height, below the conductive plate 2410. In some examples, the plates 2410 and 2412 have the same lengths, widths, and/or heights. Further, the plates 2410 may be separated by a few millimeters up to a few centimeters. A capacitive sensor 2414 is configured to measure a capacitance between the plates 2410 and 2412. The processor 120 is configured to use the capacitance values measured by the sensor 2414 to discriminate between the wet tube state and the dry tube state by determining when capacitance values change as a result of cleansing fluid in the tube 106 bridging the gap between the plates 2410 and 2412.

FIG. 24 also shows that the second side or arm 2406 of the housing 2402 includes conductive plate 2416 while the base side 2405 of the housing includes conductive plates 2418 and 2420. The conductive plates 2418 and 2420 are electrically connected to a capacitive sensor 2422, which is configured to measure capacitance between the plates 2418 and 2420. The conductive plate 2416 is configured to electrically float. The conductive plates 2418 and 2422 and sensor 2422 are configured to detect (via the processor 120) when the conductive plate 2416 is moved closer to the plates 2418 and 2422 by measuring an increase in capacitance.

FIGS. 25 and 26 show diagrams illustrating how the joint or hinge 2408 enables the second arm or side 2406 to rotate or pivot with respect to the third arm or side 2405. The example hinge 2408 may be molded as part of the housing 2402 as a living hinge. In other examples, the hinge 2408 may include a barrel hinge, a pivot hinge, a case hinge, or combinations thereof. In some instances, the hinge 2408 may be part of a member (e.g., the second arm 2406) that is configured for a desired movement upon insertion of a tube 106 into the housing 2402 of the priming sensor 104. In this embodiment, the conductive plates 2418 and 2420 may be provided on the third side 2405 of the housing 2402 that forms a base of the u-shape, whereby the hinge 2408 connects the second side 2406 to the third side 2405.

FIG. 25 shows the second side 2406 rotated, via the hinge 2408, to be parallel with the first side 2404 of the housing 2402 when the tube 106 is inserted therein. In this configuration, the conductive plate 2416 is moved closer towards the conductive plates 2418 and 2420, which causes the capacitance measured by the sensor 2422 to increase. In the illustrated example, the sensor 2422 measures the capacitance between the conductive plates 2418 and 2420. Moving the conductive plate 2416 closer towards the plates 2418 and 2420 causes the capacitance between (and around) the plates 2418 and 2420 to increase. Accordingly, the processor 120 uses output from the sensor 2422 to discriminate between a dry tube state and a no-tube state.

FIG. 26 shows an example when the tube 106 is removed from the housing 2402. In this example, the second side 2406 is rotated or pivoted at the hinge 2408 to be angled toward or be closer to the first side 2404. In this configuration, the conductive plate 2416 is moved away from the conductive plates 2418 and 2420, which causes the capacitance measured by the sensor 2422 to decrease. The movement of the second side 2406 increases an area of a gap 2600 between the conductive plates 2416, 2418, and 2420. In some embodiments, the gap 2600 may include air or a compressible foam that fills the gap between the second side 2406 and the third side 2405 of the housing 2402.

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis apparatus comprising:
  a patient tube configured to receive dialysis fluid from a source of dialysis fluid;
  at least one pump configured to move the dialysis fluid from the source to the patient tube during a priming sequence;
  a priming sensor including a housing having a recessed section configured to accept a portion of the patient tube, the recessed section of the housing including
    a first side including a first conductive plate,
    a member including a second conductive plate, the member being moveably connected to a second side of the recessed section and configured for a desired movement upon insertion of the portion of the patient tube into the housing of the priming sensor, and
    a third side opposing the first side, the third side including
      a third conductive plate disposed across from a top portion of the first conductive plate, and
      a fourth conductive plate disposed across from a bottom portion of the first conductive plate;
  a first capacitive sensor positioned and arranged to measure a first capacitance between the first conductive plate and the third conductive plate;
  a second capacitive sensor positioned and arranged to measure a second capacitance between the third conductive plate and the fourth conductive plate; and
  a processor configured to operate with the at least one pump, the first capacitive sensor, and the second capacitive sensor, the processor configured to
    use the measured second capacitance to determine a first transition between (i) a no-tube state and (ii) a dry tube state,
    use the measured first capacitance to determine a second transition between (ii) the dry tube state and (iii) a wet tube state,
    cause the at least one pump to pump the dialysis fluid through t-e the patient tube for the priming sequence after the dry tube state is determined, and
    transmit a message indicative that the patient tube is primed after the wet tube state is determined.

2. The apparatus of claim 1, wherein the priming sensor includes a third capacitive sensor positioned and arranged to measure a third capacitance between the first conductive plate and the fourth conductive plate, and
  wherein the processor is configured to combine values of the first capacitance with values of the third capacitance to determine between at least one of (i) the no-tube state and (ii) the dry tube state, or (ii) the dry tube state and (iii) the wet tube state.

3. The apparatus of claim 1, wherein the second conductive plate bends or pivots when the portion of the patient tube is inserted into the housing of the priming sensor, causing the first capacitance to increase.

4. The apparatus of claim 1, wherein the second conductive plate is at least one of (a) positioned and arranged to electrically float, or (b) formed from a conductive plastic or a conductively painted plastic.

5. The apparatus of claim 1, wherein the third conductive plate is at least one of (a) formed with a width that is equal to a width of the fourth conductive plate, or (b) spaced apart from the fourth conductive plate by a distance between 0.5 millimeters and 2 centimeters.

6. The apparatus of claim 1, wherein the first conductive plate, the third conductive plate, and the fourth conductive plate are enclosed within the recessed section of the housing of the priming sensor.

7. The apparatus of claim 1, wherein the processor is configured to determine the first transition between the no-tube state and the dry tube state by determining that a change in values of the measured second capacitance is greater than a first transition threshold, and wherein the processor is configured to determine the second transition between the dry tube state and the wet tube state by determining that a change in values of the measured first capacitance is greater than a second transition threshold.

8. The apparatus of claim 7, wherein at least one of the first transition threshold or the second transition threshold corresponds to at least a doubling of the respective values of the measured capacitance from a first value to a second value in less than 0.5 seconds, and wherein the second value is at least substantially constant for at least two seconds.

9. The apparatus of claim 1, wherein the processor is further configured such that when the wet tube state is determined, a peritoneal dialysis treatment is enabled.

10. The apparatus of claim 1, further comprising a user interface configured to display at least one of text or a graphic corresponding to the determined states (i) to (iii).

11. The apparatus of claim 1, wherein the first capacitance is indicative of a presence of the dialysis fluid within the patient tube, and
  wherein the second capacitance is indicative of a distance of the second conductive plate from the third and fourth conductive plates.

12. A sensor apparatus comprising:
a housing including a recessed section configured to accept a portion of a tube, the housing including
a first side including a first conductive plate,
a member including a second conductive plate, the member being moveably connected to a second side of the housing for detecting insertion of the portion of the tube into the housing, and
a third side opposing the first side, the third side including
a third conductive plate disposed across from a top portion of the first conductive plate, and
a fourth conductive plate disposed across from a bottom portion of the first conductive plate;
a first capacitive sensor positioned and arranged to measure a first capacitance between the first conductive plate and the third conductive plate; and
a second capacitive sensor positioned and arranged to measure a second capacitance between the third conductive plate and the fourth conductive plate.

13. The apparatus of claim 12, operable with a medical fluid delivery machine including at least one pump and a control unit operable with the first and second capacitive sensors to:
use the measured second capacitance to determine a first transition between (i) a no-tube state and (ii) a dry tube state; and
cause the at least one pump to pump a fluid through the tube to conduct a priming sequence after the dry tube state is determined.

14. The apparatus of claim 13, wherein the control unit is further configured to:
use the measured first capacitance to determine a second transition between (ii) the dry tube state and (iii) a wet tube state; and
transmit a message indicative that the tube is primed after the wet tube state is determined.

15. The apparatus of claim 14, wherein the first capacitance is indicative of a presence of fluid within the tube, and wherein the second capacitance is indicative of a distance of the second conductive plate from the third and fourth conductive plates.

16. The apparatus of claim 14, wherein the control unit is further configured to:
increment a counter each time the wet tube state is determined;
compare a value of the counter to a counter threshold; and
determine the wet tube state when the value of the counter equals or exceeds the counter threshold.

17. The apparatus of claim 13, wherein the control unit includes the first capacitive sensor and the second capacitive sensor.

18. A medical fluid delivery apparatus comprising:
a patient tube configured to receive dialysis fluid from a source of dialysis fluid;
at least one pump configured to move the dialysis fluid from the source to the patient tube during a priming sequence;
a priming sensor including a housing having a recessed section configured to accept a portion of the patient tube, the recessed section of the housing including
a first side including a first conductive plate,
a member including a second conductive plate, the member being moveably connected to a second side of the recessed section and configured for a desired movement upon insertion of the portion of the patient tube into the housing of the priming sensor, and
a third side opposing the first side, the third side including
a third conductive plate disposed across from a top portion of the first conductive plate, and
a fourth conductive plate disposed across from a bottom portion of the first conductive plate;
a first capacitive sensor positioned and arranged to measure a first capacitance between the first conductive plate and the third conductive plate;
a second capacitive sensor positioned and arranged to measure a second capacitance between the third conductive plate and the fourth conductive plate; and
a control unit configured to operate with the least one pump, the first capacitive sensor, and the second capacitive sensor, the control unit configured to perform the priming sequence.

19. The apparatus of claim 18, wherein the control unit during the priming sequence uses the measured second capacitance to determine a first transition between (i) a no-tube state and (ii) a dry tube state,
wherein the measured second capacitance is indicative of a distance of the second conductive plate from the third and fourth conductive plates.

20. The apparatus of claim 19, wherein the control unit during the priming sequence causes the at least one pump to pump the dyalysis fluid through the patient tube after the dry tube state is determined.

21. The apparatus of claim 19, wherein the control unit during the priming sequence is configured to use the measured first capacitance to determine a second transition between (ii) the dry tube state and (iii) a wet tube state,
wherein the measured first capacitance is indicative of a presence of the dialysis fluid within the patient tube.

22. The apparatus of claim 21, wherein the control unit during the priming sequence transmits a message indicative that the patient tube is primed after the wet tube state is determined.

* * * * *